(12) United States Patent
Tsubusaki et al.

(10) Patent No.: US 11,041,052 B2
(45) Date of Patent: Jun. 22, 2021

(54) BIODEGRADABLE HYDROGEL HAVING CYCLIC BENZYLIDENE ACETAL STRUCTURE

(71) Applicant: NOF CORPORATION, Tokyo (JP)

(72) Inventors: Takuma Tsubusaki, Kawasaki (JP); Mika Shishido, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 16/082,788

(22) PCT Filed: Mar. 29, 2017

(86) PCT No.: PCT/JP2017/012925
§ 371 (c)(1),
(2) Date: Sep. 6, 2018

(87) PCT Pub. No.: WO2017/170705
PCT Pub. Date: Oct. 5, 2017

(65) Prior Publication Data
US 2019/0092906 A1    Mar. 28, 2019

(30) Foreign Application Priority Data

Mar. 31, 2016  (JP) .............................. JP2016-070109

(51) Int. Cl.
| | | |
|---|---|---|
| *C08J 3/075* | (2006.01) | |
| *C08L 71/02* | (2006.01) | |
| *C08L 77/04* | (2006.01) | |
| *A61K 47/22* | (2006.01) | |
| *C08K 5/00* | (2006.01) | |
| *A61K 47/34* | (2017.01) | |
| *C08G 65/333* | (2006.01) | |
| *C08K 11/00* | (2006.01) | |

(52) U.S. Cl.
CPC ............... *C08J 3/075* (2013.01); *A61K 47/22* (2013.01); *A61K 47/34* (2013.01); *C08G 65/333* (2013.01); *C08K 5/00* (2013.01); *C08K 11/00* (2013.01); *C08L 71/02* (2013.01); *C08L 77/04* (2013.01); *C08J 2371/02* (2013.01); *C08L 2201/06* (2013.01); *C08L 2312/00* (2013.01)

(58) Field of Classification Search
CPC .................................. C08J 3/075; C08L 71/02
See application file for complete search history.

(56) References Cited

U.S. PATENT DOCUMENTS

| | | | | | |
|---|---|---|---|---|---|
| 4,670,417 | A | * | 6/1987 | Iwasaki | ................ C07K 14/805 514/13.5 |
| 5,219,564 | A | * | 6/1993 | Zalipsky | ................. A61L 15/26 424/179.1 |
| 6,899,867 | B2 | * | 5/2005 | Bentley | ................. A61K 31/765 424/78.02 |
| 2002/0064546 | A1 | | 5/2002 | Harris | |
| 2004/0076602 | A1 | * | 4/2004 | Harris | .................... A61K 47/10 424/78.38 |
| 2004/0224021 | A1 | | 11/2004 | Omidian et al. | |
| 2008/0268127 | A1 | | 10/2008 | van de Velde | |
| 2012/0027775 | A1 | * | 2/2012 | Won | ..................... A61K 9/0024 424/158.1 |
| 2012/0058943 | A1 | * | 3/2012 | Werner | ................... A61L 27/52 514/8.1 |
| 2014/0288190 | A1 | * | 9/2014 | Ashley | ............... A61K 47/6903 514/772.3 |
| 2016/0046763 | A1 | * | 2/2016 | Tsubusaki | ........... C08G 65/331 548/546 |
| 2017/0074861 | A1 | * | 3/2017 | Singh | .................. C12N 5/0012 |
| 2017/0107325 | A1 | | 4/2017 | Tsubusaki et al. | |

(Continued)

FOREIGN PATENT DOCUMENTS

| | | |
|---|---|---|
| EP | 3 279 236 A1 | 2/2018 |
| JP | 5-279416 A | 10/1993 |

(Continued)

OTHER PUBLICATIONS

Huang et al. European Polymer Journal 49 (2013) 2895-2905 (Year: 2013).*
Hutanu et al. (Mod Chem appl. 20014 2:2) (Year: 2014).*
Hutanu et al. (Mod Chem appl 2014, 2:2) (Year: 2014).*
JenKem Technology USA (https://www.jenkemusa.com/multi-arm-pegs, accessed Dec. 14, 2020) (Year: 2020).*
Dirk Steinhilber et al. "Surfactant free preparation of biodegradable dendritic polyglycerol nanogels by inverse nanoprecipitation for encapsulation and release of pharmaceutical biomacromolecules", Journal of Controlled Release, vol. 169, Elsevier, 2013, 20 pages.
Dirk Steinhilber et al. "A Microgel Construction Kit for Bioorthogonal Encapsulation and pH-Controlled Release of Living Cells**", Angewandte Communications, Wiley, vol. 52, 2013, pp. 13538-13543.

(Continued)

*Primary Examiner* — Liam J Heincer
(74) *Attorney, Agent, or Firm* — Sughrue Mion, PLLC

(57) ABSTRACT

A biodegradable hydrogel having an acetal structure whose hydrolysis rate under different pH environments in the living body can be accurately controlled. The hydrogel is obtained by crosslinking a polyalkylene glycol derivative having a cyclic benzylidene acetal structure represented by formula (1) shown below with a crosslinking agent:

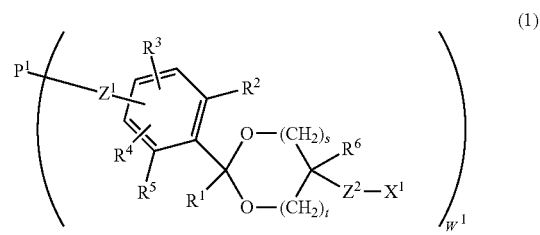

(1)

where $R^1$ and $R^6$; $R^2$, $R^3$, $R^4$ and $R^5$; s; t; s+t; $P^1$; $Z^1$ and $Z^2$; $W^1$ and $X^1$ are as defined herein.

2 Claims, 4 Drawing Sheets

(56) References Cited

U.S. PATENT DOCUMENTS

2018/0264176 A1* 9/2018 Broguiere ................ C08J 3/075
2019/0241866 A1* 8/2019 Weber .................... C12M 21/08

FOREIGN PATENT DOCUMENTS

| JP | 2001-518528 A | 10/2001 |
| JP | 2006-524742 A | 11/2006 |
| JP | 2008-531011 A | 8/2008 |
| WO | 99/14259 A1 | 3/1999 |
| WO | 2015/152182 A1 | 10/2015 |

OTHER PUBLICATIONS

International Search Report (PCT/ISA/210) dated May 30, 2017 issued by the International Searching Authority in International Application No. PCT/JP2017/012925.
Written Opinion (PCT/ISA/237) dated May 30, 2017 issued by the International Searching Authority in International Application No. PCT/JP2017/012925.
Elizabeth R. Gillies et al., "Stimuli-Responsive Supramolecular Assemblies of Linear-Dendritic Copolymers", Journal of the American Chemical Society (JACS), vol. 126, No. 38, American Chemical Society, XP008144035, Sep. 29, 2004, pp. 11936-11943.
Communication dated Nov. 4, 2019, issued by the European Patent Office in corresponding European Application No. 17775239.1.
Office Action dated Jan. 4, 2021 by the Japanese Patent Office in Japanese Patent Application No. 2017-062153.

\* cited by examiner

BIODEGRADABLE HYDROGEL HAVING CYCLIC BENZYLIDENE ACETAL STRUCTURE

CROSS REFERENCE TO RELATED APPLICATIONS

This application is a National Stage of International Application No. PCT/JP2017/012925 filed Mar. 29, 2017, claiming priority based on Japanese Patent Application No. 2016-070109 filed Mar. 31, 2016.

TECHNICAL FIELD

The present invention relates to a biodegradable hydrogel having an acetal structure, which is hydrolyzable in the living body.

BACKGROUND ART

Hydrogel is excellent in biocompatibility because the main component is water, and is attracting attention in various fields including biomaterial. In general, hydrogel is formed by three-dimensional crosslinking of a natural or synthetic hydrophilic polymer.

Examples of the hydrogel formed by crosslinking of a natural polymer include hydrogel formed from a polysaccharide or polypeptide, for example, fibrin, gelatin, agarose, collagen, hyaluronic acid, chitosan, dextran, pectin, albumin, heparin, alginic acid or polylysine.

Examples of the hydrogel formed by chemical or physical crosslinking of a synthetic polymer include hydrogels formed from polyvinyl alcohol, poly(2-hydroxyethyl methacrylate), polyacrylic acid, polyacrylamide, polyglycerol, polylactic acid, polyglycolic acid, poly(N-vinylpyrrolidone), poly(phosphazene), polyalkylene glycol, or copolymers composed of a combination thereof.

Hydrogels of synthetic polymer generally have more excellent mechanical strength than hydrogels of natural polymer, and further have an advantage in that various advanced features can be imparted to the hydrogels by changing the composition or structure of the polymer.

Of the synthetic polymers used for hydrogels, polyethylene glycol is particularly excellent in the biocompatibility because of its high hydrophilicity and low antigenicity. Further, polyethylene glycol has features of a high structural uniformity and an extremely small polydispersity so that a uniform gel structure can be constructed with good reproducibility. Therefore, the hydrogel using polyethylene glycol has high safety and is very useful as a medical hydrogel.

As to a copolymer of polyethylene glycol with polypropylene glycol or polybutylene glycol, which has higher hydrophobicity, when the composition ratio thereof is changed, swellability, flexibility, mechanical strength, cell/tissue adhesiveness and the like of the hydrogel formed using the copolymer can be arbitrarily adjusted.

Hydrogel of polyethylene glycol is utilized as a surgical sealant, for example, a hemostatic agent, a wound dressing or an antiadhesive agent. Since the hydrogel is used during surgery, an in-situ gelling method, a gelling method of spraying on the affected area with mixing or the like is used. It is required for the hydrogel to gel instantaneously, on the other hand, it is required for the hydrogel to be rapidly removed from the body once the hydrogel is no longer needed, for example, because of healing of the affected area. Since the surgical removal of the hydrogel is accompanied by not a little pain, it is required for the hydrogel to decompose in the body and to be discharged from the body. For the purpose, a biodegradable hydrogel in which a hydrolyzable ester bond is introduced into polyethylene glycol has been developed and is put to practical use as a surgical sealant.

Another application example of the hydrogel using polyethylene glycol includes a drug delivery carrier in the drug delivery system and a sustained release base or scaffold for the physiologically active substance in the regenerative medicine. It is required for the hydrogel to have function for releasing the drug encapsulated in a suitable timing or at a desired rate. Many strategies therefor utilize the environmental stimuli in each part of the body, for example, reducing environment or presence or absence of a specific enzyme for the purpose of releasing the drug, and one of which is a technique of utilizing pH.

Although pH in the living body varies depending on the site, the deviation of pH at each site is small. For example, the periphery of a tumor tissue is an acidic environment in comparison with pH 7.4 in a normal physiological environment, but is weakly acidic at pH of 6.4 to 6.9. Also, the endosome interior and lysosome interior in the cell have a lower pH, but are at pH of 5.5 to 6.0 and at pH of 4.5 to 5.0, respectively, so that the deviation of pH is small. Therefore, in the case of utilizing a hydrogel as the drug delivery carrier, for example, a nanogel, in order to stably deliver the drug to each site and to release the drug in a suitable timing, drug release rate of the hydrogel, that is, degradation rate of the hydrogel in these different pH environments must be accurately controlled.

In general, in a hydrogel having a hydrolyzable bond, in order to adjust the hydrolysis rate, a method of changing the crosslink density is taken, but the method is undesirable in some cases, because the change of crosslink density causes change in mechanical strength or network structure and the functions of the hydrogel necessary for the respective applications are impaired. Therefore, an attempt to control the degradation rate of the hydrogel has been made by adjusting hydrolysis rate of the hydrolyzable bond in place of changing the crosslink density.

Since an acetal bond is also highly sensitive to pH as well as the ester bond and is liable to be hydrolyzed, examples of biodegradable hydrogel in which an acetal bond is introduced into a hydrogel of polyalkylene glycol have been reported.

For example, in Patent Document 1, hydrogels containing a plurality of hydrolyzable bonds, that is, ester bonds or acetal bonds in the structure thereof are disclosed. It is disclosed here that the hydrolysis rate of hydrogel can be adjusted by changing the number of the methylene groups adjacent to the ester bond or acetal bond. However, by the method of changing only the number of the adjacent methylene groups, since the variable range of the hydrolysis rate of the ester bond or acetal bond is narrow, and the precise adjustment of the hydrolysis rate is difficult the hydrolysis rate of the hydrogel containing these groups cannot be accurately controlled.

Further, in Non-Patent Document 1 and Non-Patent Document 2, degradable hydrogels composed of polyglycerol containing a cyclic benzylidene acetal bond are reported. It is disclosed here that the hydrolysis rate of the acetal bond can be adjusted by changing the electron density by introducing a substituent on the benzene ring. However, since in the case of introducing a substituent to the benzene ring it is necessary to also consider the steric hindrance of the substituent, it is difficult to set the kind and position of the substituent suitable for imparting a desired hydrolysis rate to the acetal bond by the method described here alone, and it cannot be said that the hydrolysis rate is able to be accurately controlled. Further, the polyglycerol used herein has polydispersity of approximately from 1.3 to 1.5 and a broad molecular weight distribution. Therefore, the hydrogel formed by using the polyglycerol is poor in the structural uniformity, the difference in the degradation rate derived from sparseness and denseness of the crosslink density occurs, and the degradation rate cannot be sufficiently controlled.

In the degradable hydrogels composed of polyglycerol described in Non-Patent Document 1 and Non-Patent Document 2, the reaction used in the crosslinking is limited only to an azide-alkyne cycloaddition reaction. Since polyglycerol has a large number of hydroxyl groups in the molecule, when a crosslinking agent having a functional group, for example, an active ester or an active carbonate, which reacts with a hydroxyl group, is used in the formation of hydrogel, nonuniform crosslinked structure occurs. In particular, in the case where it is desired to crosslink through a degradable linker as in Non-Patent Document 1 and Non-Patent Document 2, when a crosslinking agent having, for example, an active ester or an active carbonate is used, a large number of ester bonds or carbonate bonds not through the degradable linker occur so that control of the degradation rate of the hydrogel obtained becomes difficult.

Further, when polyglycerol has a functional group which reacts with a hydroxyl group in the molecule, intramolecular or intermolecular crosslinking easily occurs and thus, such a functional group cannot be allowed to coexist in the molecule.

As described above, since a functional group which reacts with a hydroxyl group cannot be applied in the formation of hydrogel composed of polyglycerol, the use thereof is severely restricted.

Thus, although examples of hydrogel having an acetal bond in the structure are known, an example of a degradable hydrogel in which a hydrolysis rate of an acetal bond is accurately controlled is not known until now.

PRIOR ART DOCUMENT

Patent Document

Patent Document 1: WO1999/014259

Non-Patent Document

Non-Patent Document 1: J. Control. Release 2013, 169, 289-295
Non-Patent Document 2: Angew. Chem. Int. Ed. 2013, 52, 13538-13543

DISCLOSURE OF THE INVENTION

Problems that the Invention is to Solve

Although pH in the living body varies depending on the site, the deviation of pH at each site is small. Therefore, in order to hydrolyze a hydrogel at a desired degradation rate at pH of each of the sites, a hydrogel whose degradation rate can be accurately controlled is necessary.

An object of the present invention is to provide a biodegradable hydrogel whose degradation rate under different pH environments in the living body can be accurately controlled.

Means for Solving the Problems

As a result of the intensive investigations to solve the problems described above, the inventors have developed a biodegradable hydrogel having a cyclic benzylidene acetal structure whose hydrolysis rate under different pH environments in the living body can be accurately controlled.

The biodegradable hydrogel according to the invention has a feature in that it is obtained by crosslinking a polyalkylene glycol derivative in which cyclic benzylidene acetals are introduced into all terminals of the polyalkylene glycol with a crosslinking agent.

The polyalkylene glycol derivative is a compound described in WO 2015/152182, but there is no description therein as to the application of hydrogel. Therefore, the biodegradable hydrogel according to the invention is novel. In the polyalkylene glycol derivative, by appropriately selecting the kind and position of the substituent(s) on the benzene ring of the cyclic benzylidene acetal, the electron density and degree of steric hindrance around the acetal group which affect the hydrolysis rate of the acetal can be adjusted and thus, it is possible to impart a desired hydrolysis rate to the acetal.

Another feature of the invention resides in that the biodegradable hydrogel according to the invention is obtained by using a polyalkylene glycol derivative having a narrow polydispersity and crosslinking with a crosslinking agent having a narrow polydispersity or a monodispersed crosslinking agent. Thus, a hydrogel having a high structural uniformity is formed, and it is possible to decompose the hydrogel at any degradation rate in association with hydrolysis of the cyclic benzylidene acetal.

Further, since the biodegradable hydrogel according to the invention is obtained by performing crosslinking using a polyalkylene glycol derivative having a chemically reactive functional group only at the terminal through the cyclic benzylidene acetal and a crosslinking agent, crosslinking not through the cyclic benzylidene acetal does not occur so that a hydrogel having a high structural uniformity can be obtained. Therefore, it is possible to precisely control the degradation rate of the hydrogel.

As described above, the hydrogel having a high structural uniformity obtained by introducing the cyclic benzylidene acetals into all terminals of polyalkylene glycol and crosslinking the resulting polyalkylene glycol derivative with a crosslinking agent makes it possible to accurately control the decomposition rate under different pH environments in the living body.

That is, the present invention includes the following items.

[1] A hydrogel obtained by crosslinking a polyalkylene glycol derivative having a cyclic benzylidene acetal structure with a crosslinking agent, wherein the polyalkylene glycol derivative having a cyclic benzylidene acetal structure is represented by the following formula (1):

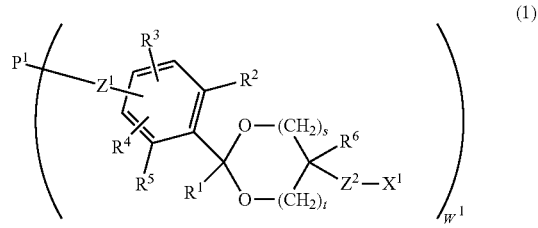

wherein, in the formula (1), $R^1$ and $R^6$ are each independently a hydrogen atom or a hydrocarbon group; $R^2$, $R^3$, $R^4$ and $R^5$ are each independently an electron-withdrawing or electron-donating substituent or a hydrogen atom; s is 1 or 2, t is 0 or 1, and s+t is 1 or 2; $P^1$ is a polyalkylene glycol having number of terminals from 2 to 8, and all terminals of the polyalkylene glycol constituting $P^1$ are connected to $Z^1$ respectively; $Z^1$ and $Z^2$ are each independently a selected divalent spacer, $W^1$ is an integer of 2 to 8 and is equal to the number of terminals of the polyalkylene glycol; and $X^1$ is a chemically reactive functional group.

[2] The hydrogel of [1], wherein $P^1$ is a polyethylene glycol having the number of terminals from 2 to 8.

[3] The hydrogel of [2], wherein $P^1$ is selected from the group consisting of formula (r1), formula (r2), formula (r3), formula (r4), formula (r5), formula (r6), formula (r7), formula (r8), formula (r9), formula (r10), formula (r11), formula (r12) and formula (r13):

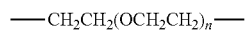
(r1)

(r2)

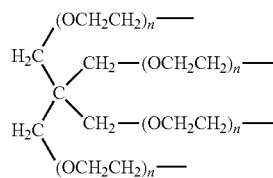
(r3)

(r4)

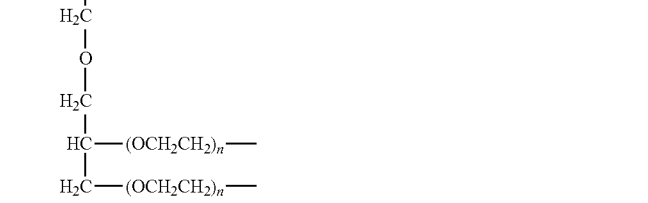

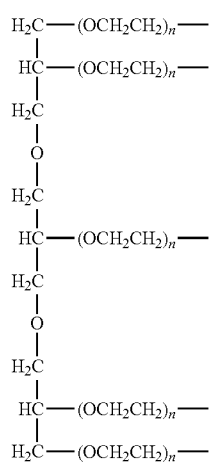
(r5)

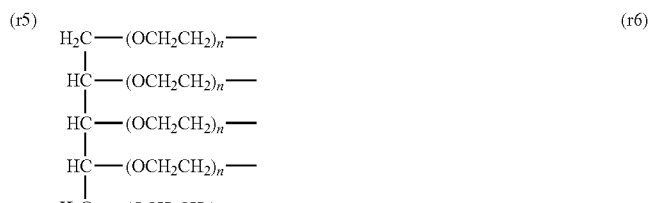
(r6)

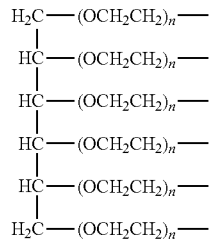
(r7)

(r8)

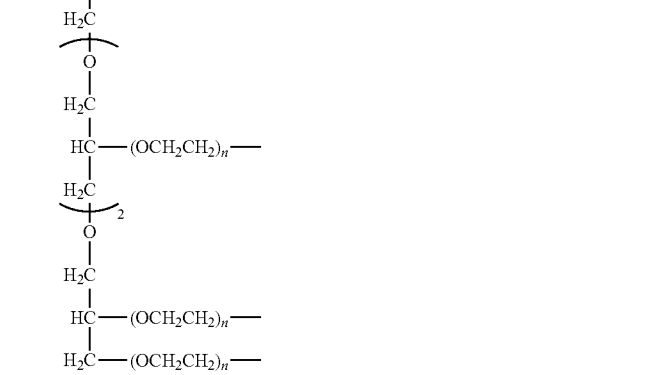

-continued

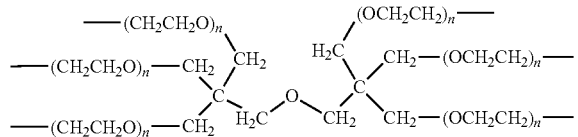
(r9)

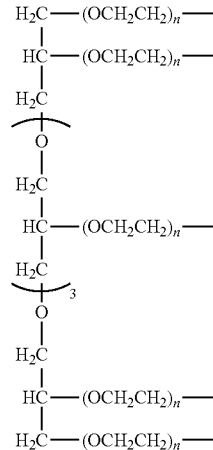
(r10)

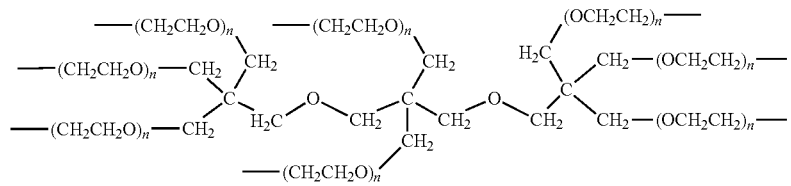
(r12)

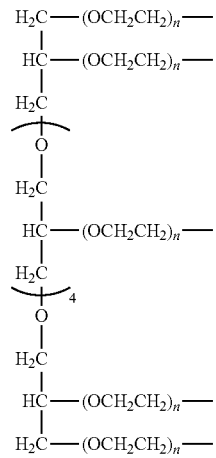

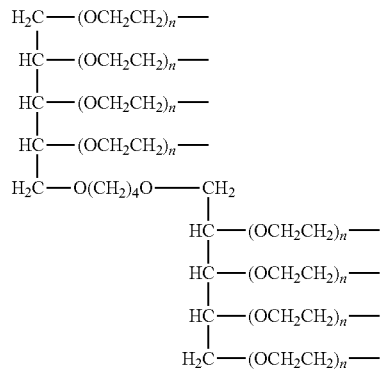
(r13)

wherein, in the formulae, n is an integer of 3 to 2,000; in a case where $P^1$ is represented by formula (r1), $W^1$ is 2; in a case where $P^1$ is represented by formula (r2), $W^1$ is 3; in a case where $P^1$ is represented by formula (r3) or formula (r4), $W^1$ is 4; in a case where $P^1$ is represented by formula (r5) or formula (r6), $W^1$ is 5; in a case where $P^1$ is represented by formula (r7), formula (r8) or formula (r9), $W^1$ is 6; in a case where $P^1$ is represented by formula (r10), $W^1$ is 7; and in a case where $P^1$ is represented by formula (r11), formula (r12) or formula (r13), $W^1$ is 8.

[4] The hydrogel of any one of [1] to [3], wherein $X^1$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[5] The hydrogel of any one of [1] to [4], wherein $Z^1$ and $Z^2$ are each independently an ether bond, an ester bond, a carbonate bond, a urethane bond, an amide bond, a secondary amino group, an alkylene group containing any of these bonds and group, a single bond or an alkylene group, and in a case where at least one of $Z^1$ and $Z^2$ is an ether bond, an ester bond, a carbonate bond, a urethane bond, an amide bond, a secondary amino group or an alkylene group containing any of these bonds and group and a plurality of identical structural units are connected, number of the structural units is 2 or less.

[6] The hydrogel of any one of [1] to [5], wherein the crosslinking agent is represented by the following formula (2):

(2)

wherein, in the formula (2), $P^2$ is a polyalkylene glycol having number of terminals from 2 to 8, and all terminals of the polyalkylene glycol constituting $P^2$ are connected to $Z^3$ respectively; $Z^3$ is a divalent spacer, $W^2$ is an integer of 2 to 8 and is equal to the number of terminals of the polyalkylene glycol; and $X^2$ is a chemically reactive functional group.

[7]
The hydrogel of [6], wherein $P^2$ is a polyethylene glycol having the number of terminals form 2 to 8.

[8]
The hydrogel of [7], wherein $P^2$ is selected from the group consisting of formula (s1), formula (s2), formula (s3), formula (s4), formula (s5), formula (s6), formula (s7), formula (s8), formula (s9), formula (s10), formula (s11), formula (s12) and formula (s13):

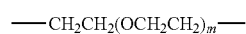
(s1)

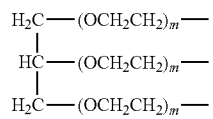
(s2)

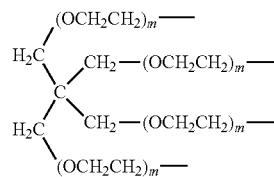
(s3)

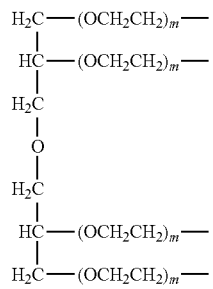
(s4)

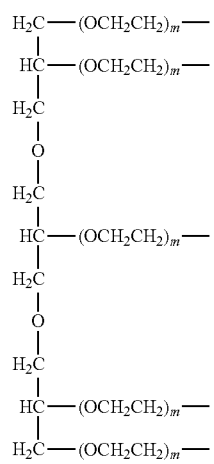
(s5)

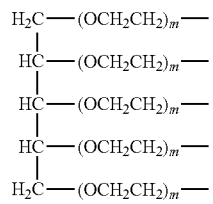
(s6)

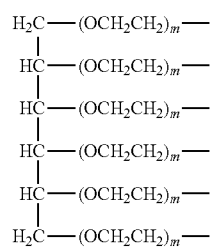
(s7)

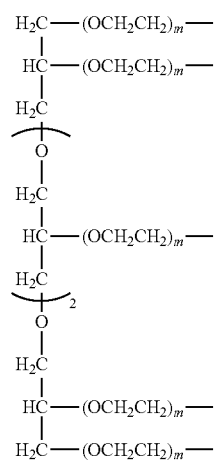
(s8)

-continued

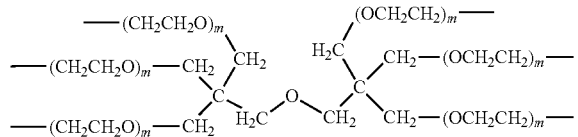
(s9)

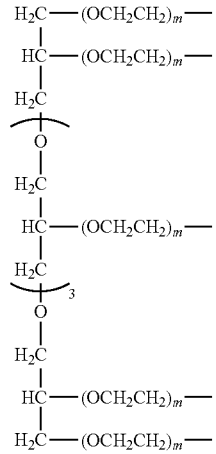
(s10)

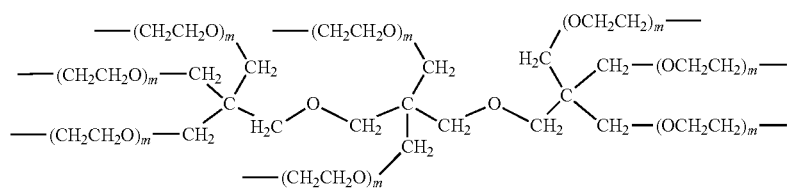
(s11)

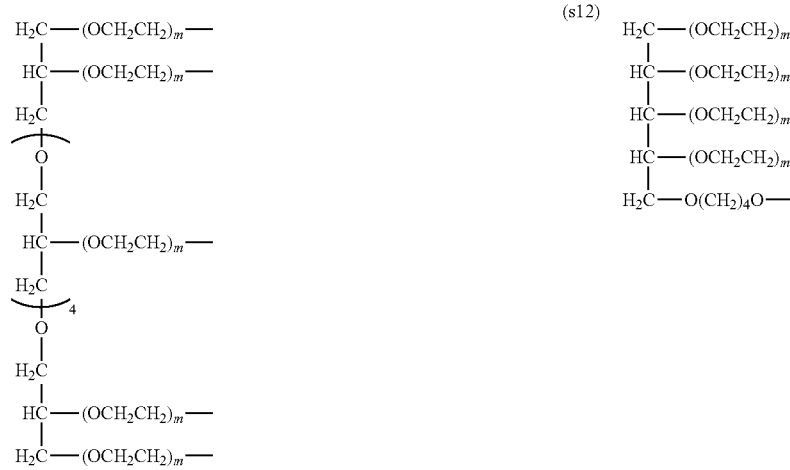
(s12)

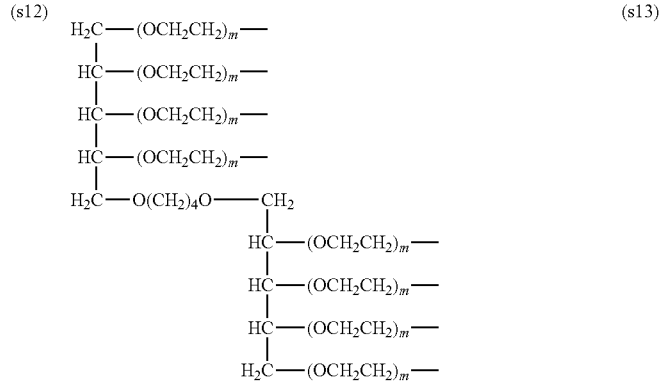
(s13)

wherein, in the formulae, m is an integer of 3 to 2,000; in a case where $P^2$ is represented by formula (s1), $W^2$ is 2; in a case where $P^2$ is represented by formula (s2), $W^2$ is 3; in a case where $P^2$ is represented by formula (s3) or formula (s4), $W^2$ is 4; in a case where $P^2$ is represented by formula (s5) or formula (s6), $W^2$ is 5; in a case where $P^2$ is represented by formula (s7), formula (s8) or formula (s9), $W^2$ is 6; in a case where $P^2$ is represented by formula (s10), $W^2$ is 7; and in a case where $P^2$ is represented by formula (s11), formula (s12) or formula (s13), $W^2$ is 8.

[9] The hydrogel of any one of [6] to [8], wherein $X^2$ is selected from the group consisting of an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

[10] The hydrogel of any one of [6] to [9], wherein $Z^3$ is an ether bond, an ester bond, a carbonate bond, a urethane bond, an amide bond, a secondary amino group, an alkylene group containing any of these bonds and group, a single bond or an alkylene group, and in a case where $Z^3$ is an ether bond, an ester bond, a carbonate bond, a urethane bond, an amide bond, a secondary amino group or an alkylene group containing any of these bonds and group and a plurality of identical structural units are connected, number of the structural units is 2 or less.

[11] The hydrogel of any one of [1] to [5], wherein the crosslinking agent is a polypeptide.

[12] The hydrogel of [11], wherein the crosslinking agent is a polypeptide having number of amino acid residues from 2 to 6.

The hydrogel of any one of [1] to [12], which further contains a biofunctional molecule.

Advantage of the Invention

The biodegradable hydrogel having a cyclic benzylidene acetal structure according to the invention makes it possible to accurately control the decomposition rate under different pH environments in the living body.

Thus, in the case wherein the biodegradable hydrogel is used in a normal physiological pH environment as a surgical sealant, for example, a hemostatic agent, a wound dressing or an antiadhesive agent, it is possible to maintain the shape of hydrogel and its function until the affected area has healed and to be rapidly degraded in the body and discharged from the body after the hydrogel is no longer needed. Further, in the case where the biodegradable hydrogel is used under a pH environment different from the normal physiological environment as a drug delivery carrier targeting to each site, for example, the periphery of a tumor tissue, endosome or lysosome, it is possible to stably deliver the drug to each site and to release the drug in a suitable timing, so that maximization of medical efficiency and reduction in side effects can be expected.

BRIEF DESCRIPTION OF THE DRAWINGS

FIG. 7 shows results of the FITC-Dextran release test with Hydrogel (37) formed by encapsulating FITC-Dextran, as a model drug, into the compound of formula (27) described in Comparative Examples performed in citrate buffer of pH 5.0 at 37° C.

MODE FOR CARRYING OUT THE INVENTION

Figure 1:
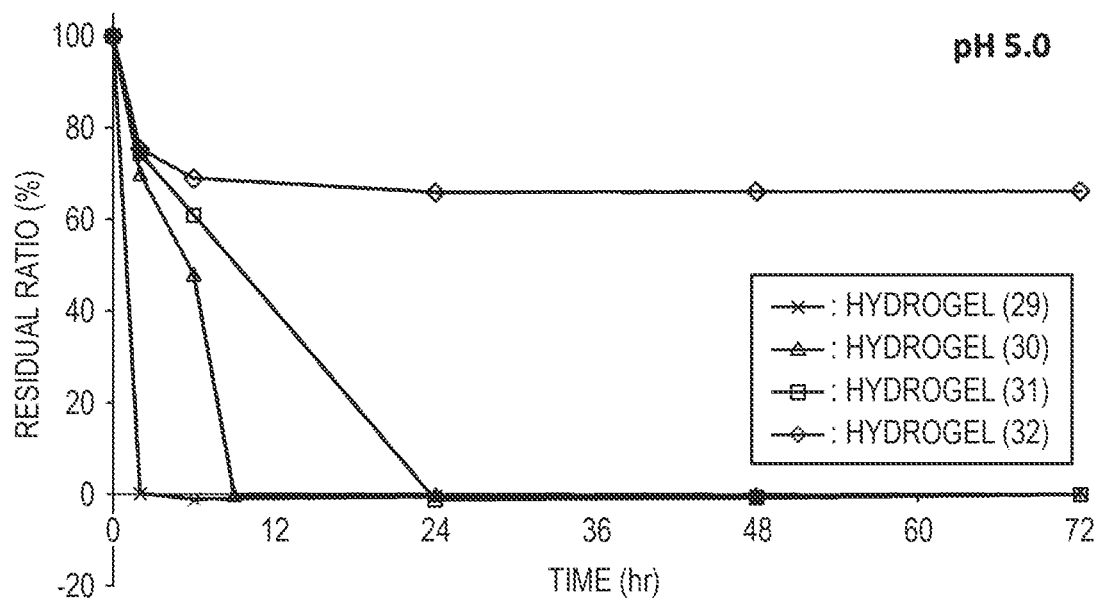
FIG. 1 shows results of the degradation test with hydrogels (29), (30), (31) and (32) each formed by using the compounds of formula (18), formula (19) and formula (20) described in Examples and the compound of formula (27) described in Comparative Examples performed in citrate buffer of pH 5.0 at 37° C.
Figure 2:
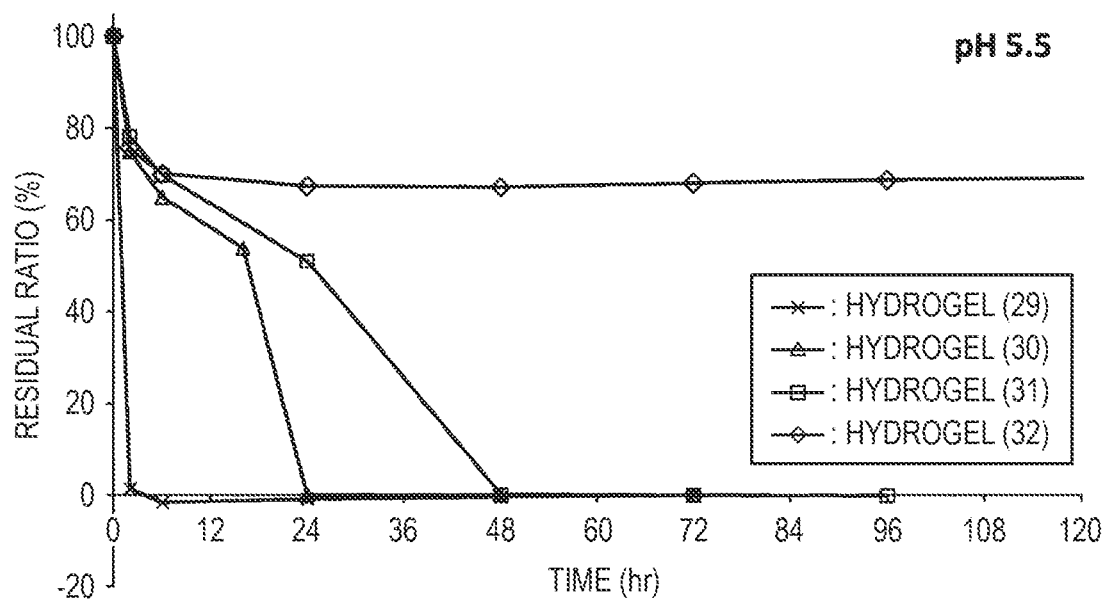
FIG. 2 shows results of the degradation test with hydrogels (29), (30), (31) and (32) each formed by using the compounds of formula (18), formula (19) and formula (20) described in Examples and the compound of formula (27) described in Comparative examples performed in citrate buffer of pH 5.5 at 37° C.
Figure 3:
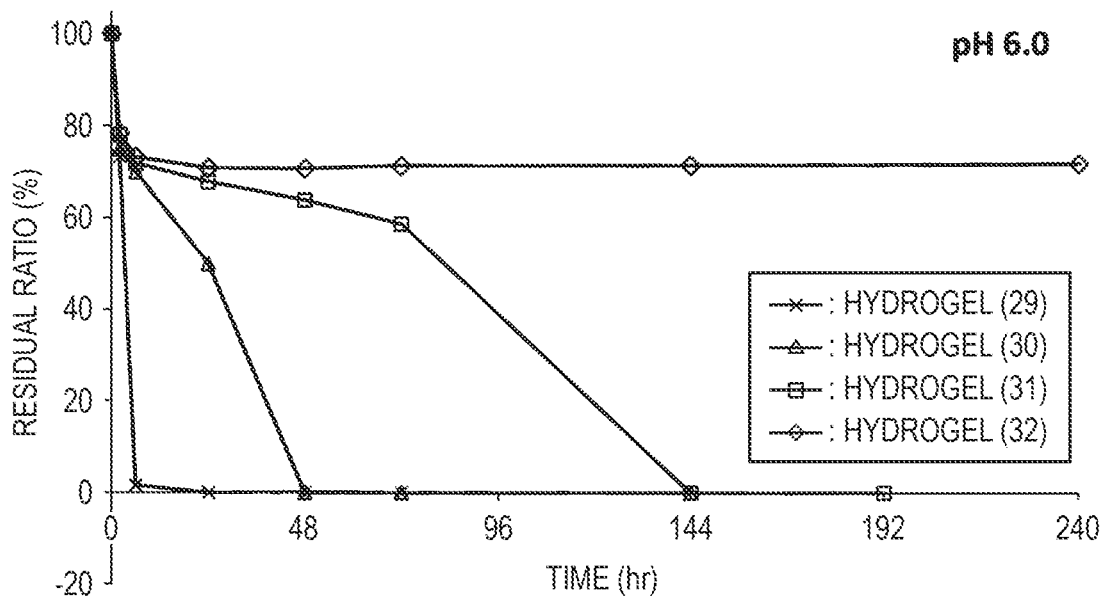
FIG. 3 shows results of the degradation test with hydrogels (29), (30), (31) and (32) each formed by using the compounds of formula (18), formula (19) and formula (20) described in Examples and the compound of formula (27) described in Comparative Examples performed in phosphate buffer of pH 6.0 at 37° C.

The invention will be described in detail hereinafter.

The term "biodegradable hydrogel" as used in the specification means a hydrogel which loses its structural integrity by being cut a chemical bond of the component under pH and temperature conditions in the living body.

The term "polydispersity" as used in the specification means a molecular weight distribution determined by using a number average molecular weight (Mn) and a weight average molecular weight (Mw) measured by gel permeation chromatography (GPC) analysis and calculating a ratio of Mw and Mn (Mw/Mn).

The polydispersity of the polyalkylene glycol derivative having a cyclic benzylidene acetal structure constituting the biodegradable hydrogel of the invention is preferably 1.15 or less, more preferably 1.12 or less, and still more preferably 1.10 or less.

The term "acetal" as used in the invention means both of an acetal structure derived from an aldehyde and an acetal structure derived from a ketone, that is, a ketal structure.

The term "cyclic acetal" as used in the invention means both of a 1,3-dioxolane structure of a 5-membered ring which is s is 1 and t is 0 in formula (1) and a 1,3-dioxane structure of a 6-membered ring which is s is 1 and t is 1 or s is 2 and t is 0 in formula (1).

Each of $R^1$ and $R^6$ in formula (1) of the invention is a hydrogen atom or a hydrocarbon group, the number of carbon atoms of the hydrocarbon group is preferably 10 or less, and specific examples of the hydrocarbon group include a methyl group, an ethyl group, a propyl group, an isopropyl group, a tert-butyl group, a phenyl group and a benzyl group. A preferred embodiment of $R^1$ is a hydrogen atom or a methyl group, and a hydrogen atom is more preferred.

The benzene ring in formula (1) of the invention may have a plurality of substituents. That is, $R^2$, $R^3$, $R^4$ and $R^5$ are each independently an electron-donating or electron-withdrawing substituent or a hydrogen atom. By appropriately selecting the kind, the position and the degree of electron-donating property and electron-withdrawing property of the substituents on the benzene ring, it is possible to adjust the electron density and degree of steric hindrance around the acetal group which affects the hydrolysis rate of the cyclic acetal. This makes it possible to impart a desired hydrolysis rate to the cyclic acetal.

The substituent which can be used in the invention is a substituent which does not inhibit an acetalization reaction of a cyclic benzylidene acetal low molecular weight compound, and a coupling reaction of the cyclic benzylidene acetal low molecular weight compound with a polyalkylene glycol intermediate in a synthesis process of the polyalkylene glycol derivative having a cyclic benzylidene acetal structure, and a terminal functional group conversion reaction of the polyalkylene glycol derivative, and further formation of hydrogel (crosslinking reaction) between the polyalkylene glycol derivative and a crosslinking agent.

The substituent may be any of electron-withdrawing substituent and electron-donating substituent as far as it satisfies the conditions described above, and the substituents may be used individually or in combination.

The electron-withdrawing substituent includes an acyl group having from 2 to 5 carbon atoms, an alkoxycarbonyl group having from 2 to 5 carbon atoms, a carbamoyl group having from 2 to 5 carbon atoms, an acyloxy group having from 2 to 5 carbon atoms, an acylamino group having from 2 to 5 carbon atoms, an alkoxycarbonylamino group having from 2 to 5 carbon atoms, a fluorine atom, a chlorine atom, a bromine atom, an iodine atom, an alkylsulfanyl group having from 1 to 4 carbon atoms, an alkylsulfonyl group having from 1 to 4 carbon atoms, an arylsulfonyl group having from 6 to 10 carbon atoms, a nitro group, a trifluoromethyl group and a cyano group, and preferred examples thereof include an acetyl group, a methoxycarbonyl group, a methylcarbamoyl group, an acetoxy group, an acetamide group, a methoxycarbonylamino group, a fluorine atom, a chlorine atom, a bromine atom, an iodine atom, a methylsulfanyl group, a phenylsulfonyl group, a nitro group, a trifluoromethyl group and a cyano group. The electron-donating substituent includes an alkyl group having from 1 to 4 carbon atoms, and preferred examples thereof include a methyl group, an ethyl group, a propyl group, an isopropyl group and a tert-butyl group. The substituent which is an electron-withdrawing group in the meta-position and an electron-donating group in the para-position or in the ortho-position includes an alkoxy group having from 1 to 4 carbon atoms, an aryl group having from 6 to 10 carbon atom and an aryloxy group having from 6 to 10 carbon atoms, and preferred examples thereof include a methoxy group, an ethoxy group, a propoxy group, an isopropoxy group, a tert-butoxy group, a phenyl group and a phenoxy group.

The kind and position of the substituent suitable for imparting a desired hydrolyzability to the polyalkylene glycol derivative having a cyclic benzylidene acetal structure represented by formula (1) can be rationally set using the method described in WO 2015/152182 by applying the Hammett's rule which quantifies the effect of the substituent on the reaction rate or equilibrium of benzene derivative in the case of para-substituted or meta-substituted benzene ring or by applying the Taft's equation which extends the Hammett's rule described above in the case of ortho-substituted benzene ring.

$X^1$ in formula (1) of the invention is not particularly limited as far as it is a functional group which forms a covalent bond upon a reaction with a functional group of a crosslinking agent. For example, the functional groups include those described in "Harris, J. M. Poly(Ethylene Glycol) Chemistry; Plenum Press: New York, 1992", "Hermanson, G. T. Bioconjugate Techniques, 2nd ed.; Academic Press: San Diego, Calif., 2008", "PEGylated Protein Drugs: Basic Science and Clinical Applications; Veronese, F. M., Ed.; Birkhauser Basel, Switzerland, 2009" and the like.

$P^1$ in formula (1) of the invention is a polyalkylene glycol having the number of terminals from 2 to 8, and all terminals of the polyalkylene glycol constituting $P^1$ are connected to $Z^1$ respectively. Specific examples of $P^1$ include polyethylene glycol, a block copolymer or random copolymer of polyethylene glycol and polypropylene glycol, a block copolymer or random copolymer of polyethylene glycol and polybutylene glycol, and a block copolymer or random copolymer of polyethylene glycol, polypropylene and polybutylene glycol.

The mass percentage of polypropylene glycol or polybutylene glycol which is higher in hydrophobicity than polyethylene glycol in the copolymer is preferably 60% or less, more preferably 50% or less, most preferably 40% or less, with respect to polyethylene glycol.

The term "polyalkylene glycol" as used in the specification means a polyalkylene glycol having a molecular weight distribution obtained by polymerization of alkylene oxide and in the case of polyethylene glycol, a monodispersed polyethylene glycol obtained by connecting of an oligoethylene glycol having a single molecular weight by a coupling reaction is also included.

In a preferred embodiment of the invention, $P^1$ in formula (1) is a polyethylene glycol having the number of terminals from 2 to 8.

In a more preferred embodiment of the invention, in the case where $P^1$ of the formula (1) is represented by formula (r1), $W^1$ is 2, in the case where $P^1$ is represented by formula (r2), $W^1$ is 3, in the case where $P^1$ is represented by formula (r3) or formula (r4), $W^1$ is 4, in the case where $P^1$ is represented by formula (r5) or formula (r6), $W^1$ is 5, in the case where $P^1$ is represented by formula (r7), formula (r8) or formula (r9), $W^1$ is 6, in the case where $P^1$ is represented by formula (r10), $W^1$ is 7, and in the case where $P^1$ is represented by formula (r11), formula (r12) or formula (r13), $W^1$ is 8.

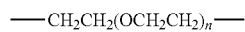

(r1)

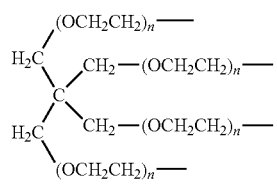

(r3)

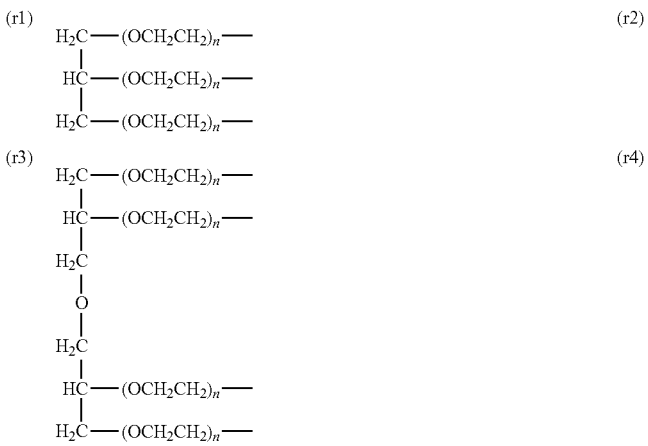

-continued
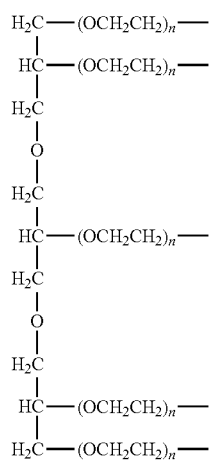
(r5)
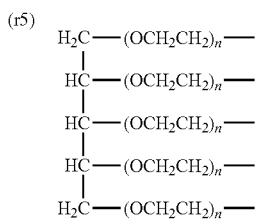
(r6)
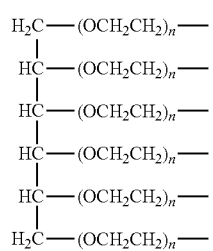
(r7)
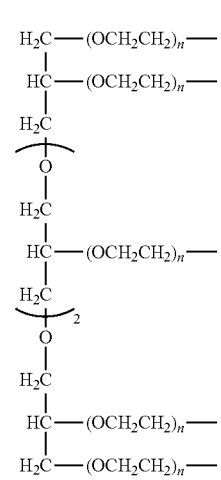
(r8)
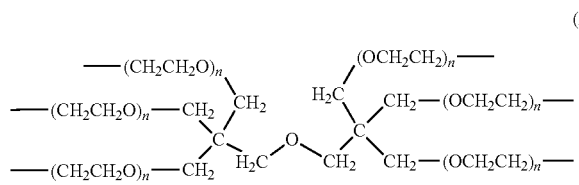
(r9)
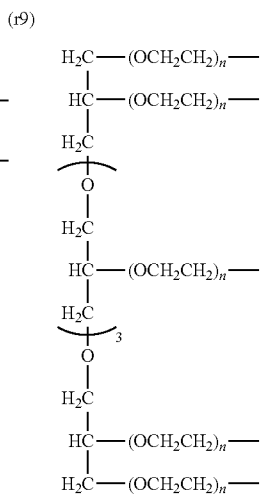
(r10)
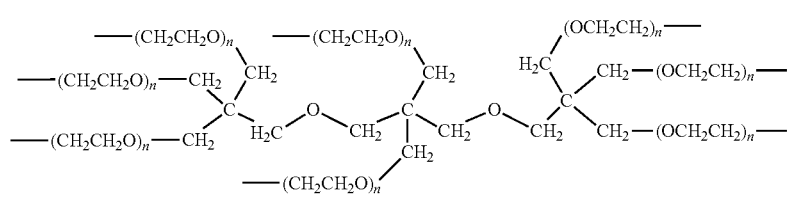
(r11)

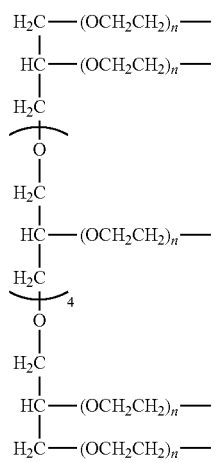
(r12)

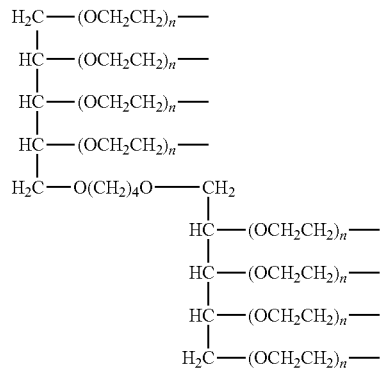
(r13)

In the formulae, n is the number of repeating units per a polyethylene glycol chain, and in the polyethylene glycol having a molecular weight distribution, it is defined that n is calculated by various theoretical calculations based on a number average molecular weight (Mn) of the compound.

A range of n in the invention is suitably an integer from 3 to 2,000, preferably an integer from 10 to 1,000, more preferably an integer from 15 to 500, and most preferably an integer from 20 to 300.

A range of a number average molecular weight (Mn) of the polyethylene glycol having the number of terminals from 2 to 8 in the invention is suitably from 500 to 90,000, preferably from 900 to 65,000, more preferably from 1,500 to 45,000, and most preferably from 3,000 to 25,000.

Preferred examples of $X^1$ in formula (1) of the invention include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group. More specifically, the functional group capable of forming a covalent bond upon a reaction with an amino group of the crosslinking agent is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the crosslinking agent is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the crosslinking agent is a thiol group, an amino group, an oxyamino group or a hydrazide group, the functional group capable of forming a covalent bond upon a reaction with an alkynyl group of the crosslinking agent is a thiol group, an amino group, an oxyamino group, a hydrazide group or an azide group, and the functional group capable of forming a covalent bond upon a reaction with an azide group of the crosslinking agent is an alkynyl group.

The term "active ester" as referred to herein indicates an activated carboxy group represented by formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents a leaving group same as described above.

In a preferred embodiment of the invention, $X^1$ is a group represented by group (I), group (II), group (III), group (IV) or group (V).

Group (I): Functional group capable of forming a covalent bond upon a reaction with an amino group of the crosslinking agent
(a), (b), (c). (d), (e) and (f) shown below:
Group (II): Functional group capable of forming a covalent bond upon a reaction with a thiol group of the crosslinking agent
(a), (b), (c), (d), (e), (f), (g), (h), (i) and (j) shown below:
Group (III): Functional group capable of forming a covalent bond upon a reaction with an aldehyde group or a carboxy group of the crosslinking agent
(g), (k), (l) and (m) shown below:
Group (IV): Functional group capable of forming a covalent bond upon a reaction with an alkynyl group of the crosslinking agent
(g), (k), (l), (m) and (n) shown below:
Group (V): Functional group capable of forming a covalent bond upon a reaction with an azide group of the crosslinking agent
(j) shown below:

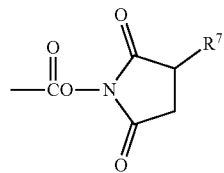
(a)

-continued

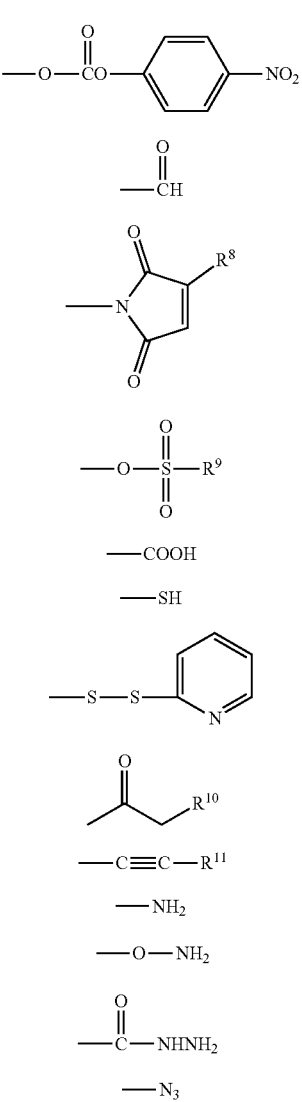

(b)
(c)
(d)
(e)
(f)
(g)
(h)
(i)
(j)
(k)
(l)
(m)
(n)

In the formulae, $R^7$ is a hydrogen atom or a sulfo group, specific examples of the sulfo group include sodium sulfonate and potassium sulfonate, and $R^7$ is preferably a hydrogen atom. $R^8$ and $R^{11}$ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. $R^9$ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and $R^9$ is preferably a methyl group, a vinyl group, a 4-methylphenyl group or a 2,2,2-trifluoroethyl group. $R^{10}$ is a halogen atom selected from a chlorine atom, a bromine atom and an iodine atom.

In formula (1) of the invention, $Z^1$ is a divalent spacer between the benzene ring of the cyclic benzylidene acetal group and the polyalkylene glycol chain, and $Z^2$ is a divalent spacer between the functional group $X^1$ and the cyclic benzylidene acetal group. These are composed of covalent bonds, are not particularly limited as far as they are more stable to hydrolysis than the cyclic benzylidene acetal group, and are preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1).

Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. However, in the case where at least one of $Z^1$ and $Z^2$ is an ether bond, an ester bond, a carbonate bond, a urethane bond, an amide bond, a secondary amino group or an alkylene group containing any of these bonds and group and a plurality of identical structural units are connected, the number of the structural units described above is 2 or less.

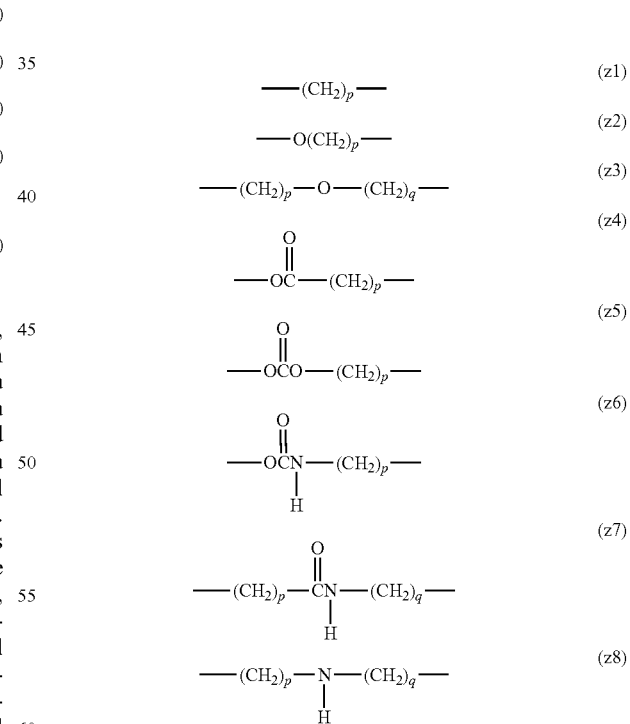

The term "crosslinking agent" as used in the invention means a molecule containing at least two functional groups each capable of forming a covalent bond with the functional group $X^1$ of the polyalkylene glycol derivative having a cyclic benzylidene acetal structure. Typically, the polyalkylene glycol derivative having a cyclic benzylidene acetal structure is soluble in water, and forms a water-insoluble hydrogel by three-dimensional crosslinking using the crosslinking agent.

In one aspect of the invention, the crosslinking agent is represented by formula (2).

$$P^2 \!-\!\!\left(Z^3 \!-\! X^2\right)_{W2} \tag{2}$$

$P^2$ in formula (2) in the aspect is a polyalkylene glycol having the number of terminals from 2 to 8, and all terminals of the polyalkylene glycol constituting $P^2$ are connected to $Z^1$ respectively. Specific examples of $P^2$ include polyethylene glycol, a block copolymer or random copolymer of polyethylene glycol and polypropylene glycol, a block copolymer or random copolymer of polyethylene glycol and polybutylene glycol, and a block copolymer or random copolymer of polyethylene glycol, polypropylene and polybutylene glycol.

The polydispersity of the crosslinking agent represented by formula (2) of the invention is preferably 1.15 or less, more preferably 1.12 or less, and still more preferably 1.10 or less.

The mass percentage of polypropylene glycol or polybutylene glycol which is higher in hydrophobicity than polyethylene glycol in the copolymer is preferably 60% or less, more preferably 50% or less, most preferably 40% or less, with respect to polyethylene glycol.

In a preferred embodiment of the aspect, $P^2$ in formula (2) is a polyethylene glycol having the number of terminals from 2 to 8.

In a more preferred embodiment of the aspect, in the case where $P^2$ of the formula (2) is represented by formula (s1), $W^2$ is 2, in the case where $P^2$ is represented by formula (s2), $W^2$ is 3, in the case where $P^2$ is represented by formula (s3) or formula (s4), $W^2$ is 4, in the case where $P^2$ is represented by formula (s5) or formula (s6), $W^2$ is 5, in the case where $P^2$ is represented by formula (s7), formula (s8) or formula (s9), $W^2$ is 6, in the case where $P^2$ is represented by formula (s10), $W^2$ is 7, and in the case where $P^2$ is represented by formula (s11), formula (s12) or formula (s13), $W^2$ is 8.

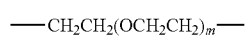
(s1)

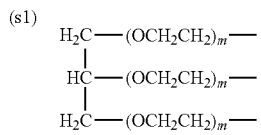
(s2)

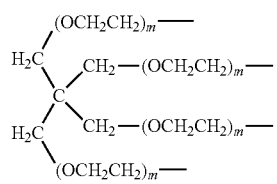
(s3)

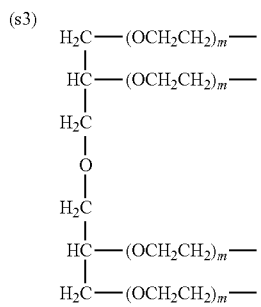
(s4)

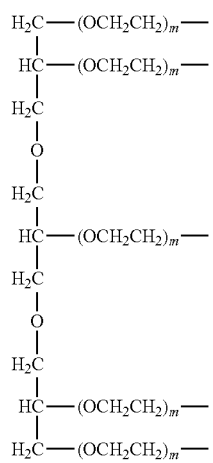
(s5)

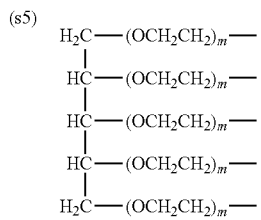
(s6)

-continued
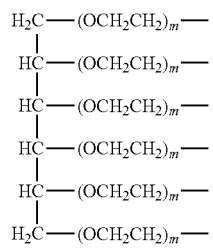
(s7)
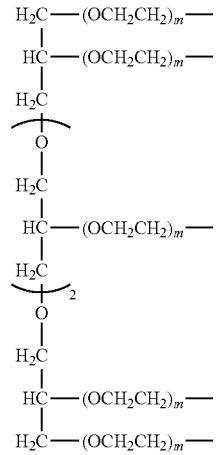
(s8)
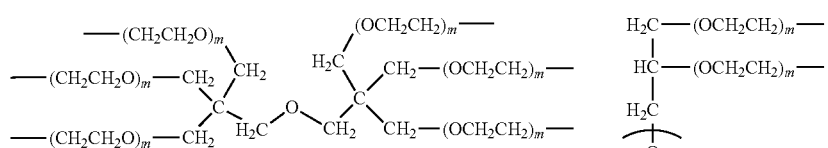
(s9)
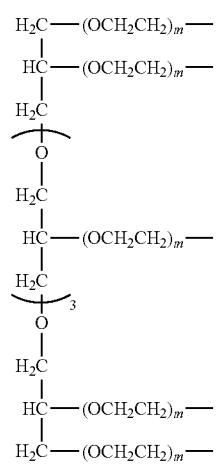
(s10)
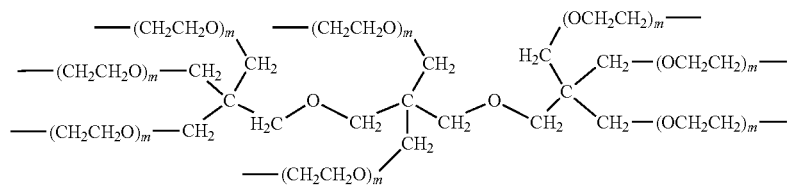
(s11)
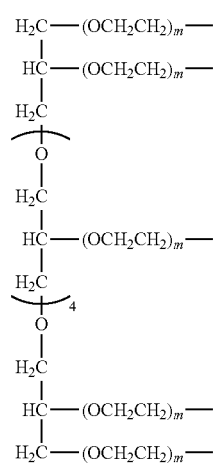
(s12)
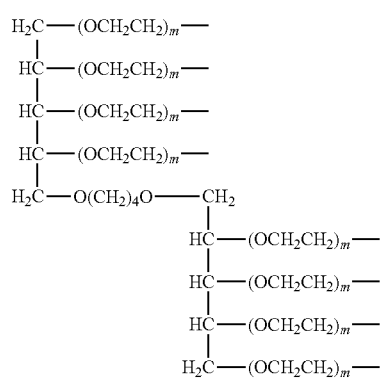
(s13)

In the formulae, m is the number of repeating units per a polyethylene glycol chain, and in the polyethylene glycol having a molecular weight distribution, it is defined that m is calculated by various theoretical calculations based on a number average molecular weight (Mn) of the compound.

A range of m in the embodiment is suitably an integer from 3 to 2,000, preferably an integer from 10 to 1,000, more preferably an integer from 15 to 500, and most preferably an integer from 20 to 300.

A range of a number average molecular weight (Mn) of the polyethylene glycol having the number of terminals from 2 to 8 in the invention is suitably from 500 to 90,000, preferably from 900 to 65,000, more preferably from 1,500 to 45,000, and most preferably from 3,000 to 25,000.

Preferred examples of $X^2$ in formula (2) of the aspect include an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group, a vinyl group, an amino group, an oxyamino group, a hydrazide group and an azide group.

More specifically, the functional group capable of forming a covalent bond upon a reaction with an amino group of the polyalkylene glycol derivative having a cyclic benzylidene acetal structure used for the biodegradable hydrogel of the invention is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, the functional group capable of forming a covalent bond upon a reaction with a thiol group of the polyalkylene glycol derivative having a cyclic benzylidene acetal structure is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group, the functional group capable of forming a covalent bond upon a reaction with an aldehyde group or a carboxy group of the polyalkylene glycol derivative having a cyclic benzylidene acetal structure is a thiol group, an amino group, an oxyamino group or a hydrazide group, the functional group capable of forming a covalent bond upon a reaction with an alkynyl group of the polyalkylene glycol derivative having a cyclic benzylidene acetal structure is a thiol group, an amino group, an oxyamino group, a hydrazide group or an azide group, and the functional group capable of forming a covalent bond upon a reaction with an azide group of the polyalkylene glycol derivative having a cyclic benzylidene acetal structure is an alkynyl group.

The term "active ester" as referred to herein indicates an activated carboxy group represented by formula: —C(=O)-L, wherein L represents a leaving group. The leaving group represented by L includes a succinimidyloxy group, a phthalimidyloxy group, a 4-nitrophenoxy group, a 1-imidazolyl group, a pentafluorophenoxy group, a benzotriazol-1-yloxy group, a 7-azabenzotriazol-1-yloxy group and the like. The term "active carbonate" as referred to herein indicates an activated carbonate group represented by formula: —O—C(=O)-L, wherein L represents a leaving group same as described above.

In a preferred embodiment of the aspect, $X^2$ is a group represented by group (I), group (II), group (III), group (IV) or group (V).

Group (I): Functional group capable of forming a covalent bond upon a reaction with an amino group of the polyalkylene glycol derivative having a cyclic benzylidene acetal structure used for the biodegradable hydrogel of the invention
(a), (b), (c), (d), (e) and (f) shown below:
Group (II): Functional group capable of forming a covalent bond upon a reaction with a thiol group of the polyalkylene glycol derivative having a cyclic benzylidene acetal structure
(a), (b), (c), (d), (e), (f), (g), (h), (i) and (j) shown below:
Group (III): Functional group capable of forming a covalent bond upon a reaction with an aldehyde group or a carboxy group of the polyalkylene glycol derivative having a cyclic benzylidene acetal structure
(g), (k), (l) and (m) shown below:
Group (IV): Functional group capable of forming a covalent bond upon a reaction with an alkynyl group of the polyalkylene glycol derivative having a cyclic benzylidene acetal structure
(g), (k), (l), (m) and (n) shown below:
Group (V): Functional group capable of forming a covalent bond upon a reaction with an azide group of the polyalkylene glycol derivative having a cyclic benzylidene acetal structure
(j) shown below:

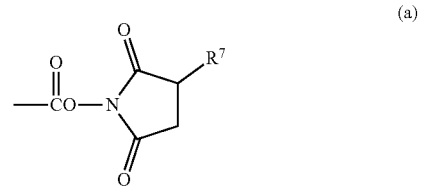

(a)

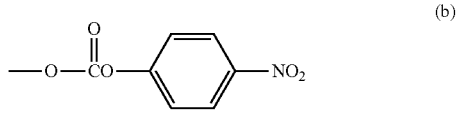

(b)

(c)

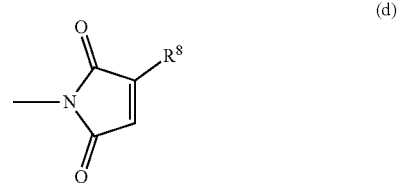

(d)

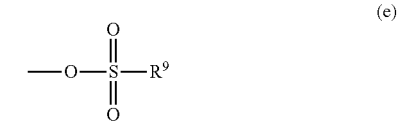

(e)

—COOH (f)

—SH (g)

(h)

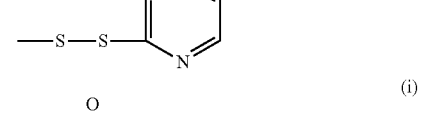

(i)

—C≡C—R¹¹ (j)

—NH₂ (k)

—O—NH₂ (l)

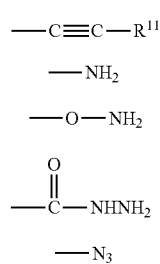
(m)

—N₃ (n)

In the formulae, R⁷ is a hydrogen atom or a sulfo group, specific examples of the sulfo group include sodium sulfonate and potassium sulfonate, and R⁷ is preferably a hydrogen atom. R⁸ and R¹¹ are each a hydrogen atom or a hydrocarbon group having from 1 to 5 carbon atoms, and specific examples of the hydrocarbon group include a methyl group, an ethyl group, a propyl group, an isopropyl group, a butyl group, a tert-butyl group and a pentyl group. R⁹ is a hydrocarbon group having from 1 to 10 carbon atoms which may contain a halogen atom, specific examples of the hydrocarbon group include a methyl group, an ethyl group, a propyl group, an isopropyl group, a butyl group, a tert-butyl group, a pentyl group, an isopentyl group, a hexyl group, a benzyl group, a 4-methylphenyl group, a trifluoromethyl group, a 2,2,2-trifluoroethyl group, a 4-(trifluoromethoxy)phenyl group, a vinyl group, a chloroethyl group, a bromoethyl group and an iodoethyl group, and R⁹ is preferably a methyl group, a vinyl group, a 4-methylphenyl group or a 2,2,2-trifluoroethyl group. R¹⁰ is a halogen atom selected from a chlorine atom, a bromine atom and an iodine atom.

Z³ in formula (2) of the aspect is a divalent spacer. This is composed of covalent bonds, is not particularly limited as far as it is more stable to hydrolysis than the cyclic benzylidene acetal group included in the biodegradable hydrogel of the invention, and is preferably an ether bond, an ester bond, a carbonate bond, a urethane bond, an amide bond, a secondary amino group, an alkylene group containing any of these bonds and group, a single bond or an alkylene group. The number of carbon atoms of the alkylene group is preferably from 1 to 24. By way of illustration and without limitation, preferred examples of the alkylene group include structures such as (z1).

Preferred examples of the alkylene group having an ether bond include structures such as (z2) or (z3). Preferred examples of the alkylene group having an ester bond include structures such as (z4). Preferred examples of the alkylene group having a carbonate bond include structures such as (z5). Preferred examples of the alkylene group having a urethane bond include structures such as (z6). Preferred examples of the alkylene group having an amide bond include structures such as (z7). Preferred examples of the alkylene group having a secondary amino group include structures such as (z8). In a preferred embodiment, p and q are each independently an integer of 1 to 12. However, in the case where Z³ is an ether bond, an ester bond, a carbonate bond, a urethane bond, an amide bond, a secondary amino group or an alkylene group containing any of these bonds and group and a plurality of identical structural units are connected, the number of the structural units described above is 2 or less.

—(CH₂)ₚ— (z1)

—O(CH₂)ₚ— (z2)

—(CH₂)ₚ—O—(CH₂)_q— (z3)

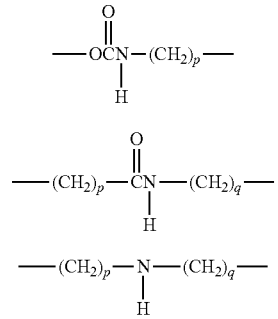
(z4)

(z5)

(z6)

(z7)

—(CH₂)ₚ—N—(CH₂)_q— (z8)
         |
         H

In the invention, the hydrogel is spontaneously formed by mixing the polyalkylene glycol derivative having a cyclic benzylidene acetal structure with the crosslinking agent or is formed by further addition of a radical initiator, a metal catalyst or the like or by external stimuli, for example, UV light irradiation. The conditions required to form the hydrogel are determined according to a combination of the functional group X¹ of the polyalkylene glycol derivative having a cyclic benzylidene acetal structure and the functional group of the crosslinking agent.

For example, in the case where X¹ is a nucleophilic functional group and the functional group of the crosslinking agent is an electrophilic functional group, the formation of hydrogel spontaneously proceeds by simple mixing. In preferred specific examples, in the case where X¹ is an amino group, an aminooxy group or a hydrazide group and the functional group of the crosslinking agent is an active ester group, an active carbonate group, an aldehyde group, an isocyanate group, an isothiocyanate group, an epoxy group, a maleimide group, a vinyl sulfone group or an acryl group, the formation of hydrogel spontaneously proceeds by simple mixing. In the case where X¹ is a thiol group and the functional group of the crosslinking agent is an active ester group, an active carbonate group, an isocyanate group, an isothiocyanate group, an epoxy group, a maleimide group, a vinyl sulfone group, an acryl group, a dithiopyridyl group or an α-haloacetyl group, the formation of hydrogel spontaneously proceeds by simple mixing.

Further, in the case where X¹ is an acryl group or a thiol group and the functional group of the crosslinking agent is a vinyl group, an alkynyl group or an allyl group, the formation of hydrogel proceeds by addition of a radical initiator, for example, an organic peroxide or UV light irradiation in the presence of a photoinitiator.

Moreover, in the case where X¹ is an azido group and the functional group of the crosslinking agent is an alkynyl group, the formation of hydrogel proceeds by a click reaction using copper (I) ion as a catalyst. However, in the case of using an alkyne having a high reactivity, for example, dibenzocyclooctyne (DBCO), the copper (I) ion my not be used.

In the invention, the bond formed by the crosslinking reaction between the polyalkylene glycol derivative having a cyclic benzylidene acetal structure and the crosslinking agent is preferably a urethane bond, an amide bond, a thioether bond, an ester bond, a disulfide bond, an ether bond, a carbonate bond, an imino bond or a 1H-1,23-triazole-1,4-diyl group, more preferably a urethane bond, an amide bond, a thioether bond, an ester bond or a disulfide bond, and still more preferably a urethane bond, an amide bond or a thioether bond.

In the invention, the hydrogel formation reaction can be performed in various suitable solvents, specifically, water, an alcohol, acetonitrile, N,N-dimethylformamide, dimethylsulfoxide or tetrahydrofuran, and preferably in an aqueous medium.

By way of illustration and without limitation, as to examples of the specific combination of the number of terminals of the polyalkylene glycol derivative having a cyclic benzylidene acetal structure and the number of terminals of the crosslinking agent in the invention, in the case where the number of terminals of the polyalkylene glycol derivative having a cyclic benzylidene acetal structure is 2, the number of terminals of the crosslinking agent is preferably 8, 4 or 3, more preferably 8 or 4, and still more preferably 8.

In the case where the number of terminals of the polyalkylene glycol derivative having a cyclic benzylidene acetal structure is 3, the number of terminals of the crosslinking agent is preferably 8, 4 or 3, more preferably 8 or 4, and still more preferably 8. In the case where the number of terminals of the polyalkylene glycol derivative having a cyclic benzylidene acetal structure is 4, the number of terminals of the crosslinking agent is preferably 8, 4, 3 or 2, more preferably 8, 4 or 3, and still more preferably 8 or 4. In the case where the number of terminals of the polyalkylene glycol derivative having a cyclic benzylidene acetal structure is 5, the number of terminals of the crosslinking agent is preferably 8, 4, 3 or 2, more preferably 8, 4 or 3, and still more preferably 8 or 4.

In the case where the number of terminals of the polyalkylene glycol derivative having a cyclic benzylidene acetal structure is 6, the number of terminals of the crosslinking agent is preferably 8, 4, 3 or 2, more preferably 8, 4 or 3, and still more preferably 8 or 4. In the case where the number of terminals of the polyalkylene glycol derivative having a cyclic benzylidene acetal structure is 7, the number of terminals of the crosslinking agent is preferably 8, 4, 3 or 2, more preferably 8, 4 or 3, and still more preferably 8 or 4. In the case where the number of terminals of the polyalkylene glycol derivative having a cyclic benzylidene acetal structure is 8, the number of terminals of the crosslinking agent is preferably 8, 4, 3 or 2, more preferably 8, 4 or 3, and still more preferably 8 or 4.

In another aspect of the invention, the crosslinking agent is polypeptide.

The term "polypeptide" as referred to herein is a monodispersed molecule in which a plurality of amino acids or amino acid derivatives are connected through peptide bonds, and specifically includes a naturally derived polypeptide, a polypeptide obtained by linking a single amino acid in a strict sequence by a technique of peptide synthesis typified by solid-phase synthesis and a pseudo-peptide and peptide mimetic including a covalent bond other than the peptide bond. The amino acid included in the peptide may be D-form or L-form.

The polypeptide of the aspect may be a linear, branched or star-shaped polypeptide.

In a preferred embodiment of the aspect, the number of the amino acid residue of the polypeptide is preferably from 2 to 6, more preferably from 2 to 5, and still more preferably from 2 to 4.

The polypeptide of the aspect is a polypeptide having at least two functional groups capable of forming a covalent bond with the functional group $X^1$ of the polyalkylene glycol derivative having a cyclic benzylidene acetal structure. It is preferably a polypeptide containing two or more amino acids or amino acid derivatives containing an amino group, a guanidino group, an imidazole group or a thiol group in the side chain, more preferably a polypeptide containing two or more amino acids selected from the group consisting of lysine, arginine, histidine and cysteine, and still more preferably a polypeptide containing two or more lysines or cysteines. It is most preferably dilysine, trilysine or tetralysine.

In the aspect, as to examples of a preferred combination of the functional group of the polypeptide and the functional group $X^1$ of the polyalkylene glycol derivative having a cyclic benzylidene acetal structure, in the case where the functional group of the polypeptide is an amino group, a guanidino group or an imidazole group, the functional group $X^1$ is an active ester group, an active carbonate group, an aldehyde group, an isocyanate group, an isothiocyanate group, an epoxy group, a maleimide group, a vinyl sulfone group, an acryl group, a sulfonyloxy group or a carboxy group, in the case where the functional group of the polypeptide is a thiol group, the functional group $X^1$ is an active ester group, an active carbonate group, an aldehyde group, an isocyanate group, an isothiocyanate group, an epoxy group, a maleimide group, a vinyl sulfone group, an acryl group, a sulfonyloxy group, a carboxy group, a thiol group, a dithiopyridyl group, an α-haloacetyl group, an alkynyl group, an allyl group or a vinyl group.

The polypeptide may be a salt, and as to specific examples thereof, in the case where the functional group included in the side chain is an amino group, a guanidino group or an imidazole group, the salt is a hydrochloride, hydrobromide or trifluoroacetate.

In another preferred embodiment of the aspect, the polypeptide is a protein. The protein is a protein having on the surface of three-dimensional structure thereof at least two functional groups capable of forming a covalent bond with the functional group $X^1$ of the polyalkylene glycol derivative having a cyclic benzylidene acetal structure, and preferred examples thereof include serum albumin, protein, for example, other serum proteins or serum concentrate, recombinant protein of serum proteins, collagen and recombinant protein of collagen.

In a preferred embodiment of the invention, the polyalkylene glycol derivative having a cyclic benzylidene acetal structure and the crosslinking agent can be mixed in a state of dissolving in an aqueous medium respectively. The aqueous medium for dissolving the polyalkylene glycol derivative having a cyclic benzylidene acetal structure is preferably a buffer having pH of 5 to 12, more preferably a buffer having pH of 6 to 11 and still more preferably a buffer having pH of 7 to 10. The aqueous medium for dissolving the crosslinking agent is preferably a buffer having pH of 3 to 12, more preferably a buffer having pH of 4 to 11 and still more preferably a buffer having pH of 5 to 10.

In the invention, the crosslink density of the hydrogel is controlled by the total molecular weight of the polyalkylene glycol derivative having a cyclic benzylidene acetal structure and the crosslinking agent and the number of effective functional groups per one molecule.

As to specific examples, a hydrogel obtained by crosslinking a polyalkylene glycol derivative having a cyclic benzylidene acetal structure and a molecular weight of 10,000 provides a high crosslink density in comparison with a hydrogel obtained by crosslinking a polyalkylene glycol derivative having a cyclic benzylidene acetal structure, the same terminal number and a molecular weight of 20,000, and using the same crosslinking agent. Further, a hydrogel obtained by crosslinking a polyalkylene glycol derivative having a cyclic benzylidene acetal structure and the number of terminals of 8 provides a high crosslink density in comparison with a hydrogel obtained by crosslinking a polyalkylene glycol derivative having a cyclic benzylidene acetal structure, the same molecular weight and the number of terminals of 4 and using the same crosslinking agent. Similarly, a hydrogel obtained by crosslinking with a crosslinking agent having a molecular weight of 10,000 provides a high crosslink density in comparison with a hydrogel obtained by crosslinking with a crosslinking agent having a molecular weight of 20,000 and the same number of terminals, and using the same polyalkylene glycol derivative having a cyclic benzylidene acetal structure. Further, a hydrogel obtained by crosslinking with a crosslinking agent having the number of terminals of 8 provides a high crosslink density in comparison with a hydrogel obtained by crosslinking with a crosslinking agent having the number of terminals of 4 and the same molecular weight, and using the same polyalkylene glycol derivative having a cyclic benzylidene acetal structure.

The crosslink density of the hydrogel in the invention is also controlled by a mass percentage of the respective compounds in a solution obtained by dissolving the polyalkylene glycol derivative having a cyclic benzylidene acetal structure and a solution obtained by dissolving the crosslinking agent in the formation of hydrogel. Specifically, as the mass percentage increases, the probability of reaction between the functional group $X^1$ of the polyalkylene glycol derivative having a cyclic benzylidene acetal structure and the functional group of the crosslinking agent in the formation of hydrogel increases, and as a result, a high crosslink density is achieved. The mass percentage of the total polyalkylene glycol derivative having a cyclic benzylidene acetal structure and crosslinking agent in the hydrogel formed is from 1 to 50%, preferably from 2 to 40%, and more preferably from 3 to 30%.

A still another method to control the crosslink density of the hydrogel in the invention is stoichiometric adjustment of the functional group $X^1$ of the polyalkylene glycol derivative having a cyclic benzylidene acetal structure and the functional group of the crosslinking agent. A molar equivalent ratio of the functional group of the crosslinking agent to the number of moles of the functional group $X^1$ in the hydrogel is preferably from 0.5 to 1.5, more preferably from 0.8 to 1.2, and still more preferably from 0.9 to 1.1.

In still another aspect of the invention, the hydrogel may further contain one or more biofunctional molecules.

The biofunctional molecule of the aspect mainly includes a biofunctional molecule, for example, protein drug, polypeptide, enzyme, antibody, antibody medicine, gene, nucleic acid compound including oligo nucleic acid and the like, nucleic acid medicine, anticancer agent and low molecular weight drug. Further, a carrier in a drug delivery system, for example, a liposome or a polymer micelle containing the biofunctional molecule, and other materials and devices for diagnosis may be contained. The biofunctional molecule may also be any compound having clinical use or a mixture thereof, any drug providing a treatment or prevention effect, a compound influencing or concerning tissue growth, cell growth or cell differenciation, an antiadhesive compound, a compound capable of inducing a biological effect, for example, immune response, or a compound playing any other roles in one or more biological processes.

In a preferred embodiment of the aspect, the biofunctional molecule may be an antiadhesive agent, an antimicrobial agent, an analgesic, an antipyretic, an anesthetic, an antiepileptic, an antihistamine, an anti-inflammatory agent, a cardiovascular drug, a diagnostic agent, a sympathomimetic agent, a cholinergic agonist, an antimuscarinic agent, an anticonvulsant, a hormone, a growth factor, a muscle relaxant, an adrenergic neuron blocking agent, an anti-tumor agents, an immunogenic agent, an immunosuppressive agent, a gastrointestinal drug, a diuretic, a steroid, a lipid, a lipopolysaccharide, a polysaccharide, a platelet activating agent, a coagulation factor or an enzyme. These bio-functional molecules can also be used in combination.

In a preferred embodiment of the aspect, by forming a hydrogel in the presence of a biofunctional molecule, the biofunctional molecule may be simply contained in a pore of the hydrogel, and a release rate of the biofunctional molecule is controlled by the degradation rate of the hydrogel.

In another preferred embodiment of the aspect, the biofunctional molecule is connected with the functional group $X^1$ of the polyalkylene glycol derivative having a cyclic benzylidene acetal structure by a covalent bond. In this case, due to the connection with the functional group $X^1$ the biofunctional molecule is connected with a polyalkylene glycol backbone of the hydrogel through the cyclic benzylidene acetal structure. In this case, a release rate of the biofunctional molecule is controlled by two factors of the degradation rate of the cyclic benzylidene acetal structure forming the hydrogel and the degradation rate of the hydrogel itself.

The formation of bond between the functional group $X^1$ of the polyalkylene glycol derivative having a cyclic benzylidene acetal structure and the biofunctional molecule can be performed as described below.

For example, the number of the functional groups of the crosslinking agent to be reacted with the functional group $X^1$ of the polyalkylene glycol derivative is adjusted to less than the number of the functional group $X^1$, a hydrogel is formed by a crosslinking reaction to remain the functional group $X^1$ which is not involved in the crosslinking reaction, and the remaining functional group $X^1$ is allowed to react with the biofunctional molecule. Alternatively, a part of the functional group $X^1$ of the polyalkylene glycol derivative having a cyclic benzylidene acetal structure is reacted in advance with the biofunctional molecule, and then the resulting reactant is mixed with the crosslinking agent to cause a crosslinking reaction between the unreacted functional group $X^1$ and the crosslinking agent, thereby forming a hydrogel.

In the aspect, a molar equivalent ratio of the functional group of the crosslinking agent to the number of moles of the functional group $X^1$ in the hydrogel is preferably from 0.5 to 0.99, more preferably from 0.6 to 0.95, and still more preferably from 0.7 to 0.9. Further, a total molar equivalent ratio of the functional groups of the crosslinking agent and the functional groups of the biofunctional molecule to the number of moles of the functional group $X^1$ in the hydrogel is preferably from 0.71 to 1.2, more preferably from 0.75 to 1.1, and still more preferably from 0.8 to 1.0.

The polyalkylene glycol derivative having a cyclic benzylidene acetal structure for use in the biodegradable hydrogel of the invention can be synthesized by performing a coupling reaction between a cyclic benzylidene acetal low molecular weight compound having a substituent and a polyalkylene glycol intermediate. The bond generated by the coupling reaction is determined by a combination of the functional groups used in the reaction, and is the ether bond, the ester bond, the carbonate bond, the urethane bond, the amide bond, the secondary amino group, the alkylene group containing any of these bonds and group, the single bond or the alkylene group contained in the divalent spacer $Z^1$ described above. In the polyalkylene glycol derivative synthesized, the terminal functional group is chemically converted, if desired. As the reaction used for the functional group conversion, a conventionally known method can be used, but it is necessary to appropriately select conditions which do not decompose the cyclic benzylidene acetal group of formula (1) and the bonds contained in the divalent spacers $Z^1$ and $Z^2$ described above.

As a typical example of performing the coupling reaction between the cyclic benzylidene acetal low molecular weight compound and the polyalkylene glycol intermediate and further the chemical conversion of the terminal functional group, the steps described below are exemplified. The description will be made herein using polyethylene glycol having the number of terminals of 4 as an example.

(A) Synthesis of Cyclic Benzylidene Acetal Low Molecular Weight Compound

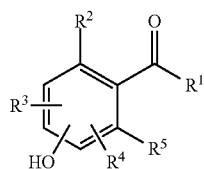

(3)

in the formula, $R^1$ is a hydrogen atom or a hydrocarbon group; and $R^2$, $R^3$, $R^4$ and $R^5$ are each independently an electron-withdrawing or electron-donating substituent or a hydrogen atom.

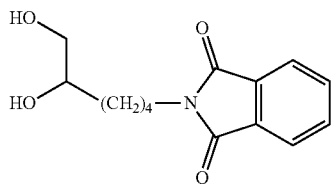

(4)

A carbonyl compound of formula (3) having a hydroxyl group which is a chemically reactive functional group is allowed to react with a 1,2-diol derivative of formula (4) having a phthalimide group in which an amino group is protected with a phthaloyl group in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an acid catalyst to obtain a compound of formula (5) shown below having a cyclic benzylidene acetal group. The resulting compound may be purified by extraction, recrystallization, adsorbent treatment, column chromatography or the like. In place of the carbonyl compound, it is possible to use a corresponding acetal derivative of a lower alcohol. The lower alcohol is preferably an alcohol having from 1 to 5 carbon atoms, and more preferably methanol or ethanol. The acid catalyst may be either an organic acid or an inorganic acid and is not particularly limited, and specific examples thereof include p-toluenesulfonic acid, pyridinium p-toluenesulfonate, methanesulfonic acid, 10-camphorsulfonic acid, hydrogen chloride, iodine, ammonium chloride, oxalic acid, boron trifluoride-diethyl ether complex and the like.

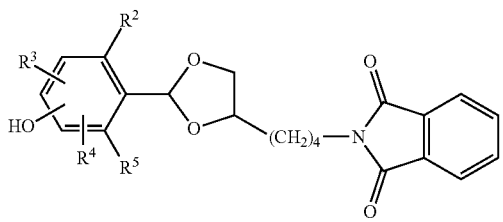

(5)

The "protective group" as referred to herein is a component which prevents or blocks a reaction of a specific chemically reactive functional group in a molecule under certain reaction conditions. The protective group varies depending on the kind of the chemically reactive functional group to be protected, the conditions to be used and the presence of the other functional group or protective group present in the molecule. Specific examples of the protective group can be found in many general books and are described, for example, in "Wuts, P. G. M.; Greene, T. W., Protective Groups in Organic Synthesis, 4th ed.; Wiley-Interscience: New York, 2007". Moreover, the functional group protected by the protective group can reproduce the original functional group by deprotection using reaction conditions suitable for each of the protective groups, that is, causing a chemical reaction. Therefore, in the specification, a functional group which is protected by a protective group and is capable of being deprotected by various reactions is included in the "chemically reactive functional group". The typical deprotection conditions of the protective group are described in the literature described above.

As the chemically reactive functional group in the compound of formula (3), a functional group other than the hydroxyl group can also be used. Specific examples thereof include a hydroxyalkyl group, an amino group, an aminoalkyl group, a carboxy group and a carboxyalkyl group. Further, the functional group described above may be protected by a protective group which is stable in the acidic conditions of the acetalization reaction and can be deprotected under reaction conditions other than catalytic reduction by which the cyclic benzylidene acetal group is decomposed. As to preferred combinations of the functional group to be protected and the protective group, when the functional group to be protected is a hydroxyl group or a hydroxyalkyl group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is an amino group or an aminoalkyl group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group.

When the functional group to be protected is a carboxy group or a carboxyalkyl group, for example, an alkyl ester protective group and a silyl ester protective group are exemplified, and specific examples thereof include a methyl group, a 9-fluorenylmethyl group and a tert-butyldimethylsilyl group. The kinds and the typical deprotection conditions of the specific protective groups are described in the literature described above, and the reaction conditions suitable for each of the protective groups are selected and the deprotection can be performed before the reaction with the hydrophilic polymer intermediate.

Moreover, as the chemically reactive functional group excepting the 1,2-diol moiety in the compound of formula (4), a functional group other than the phthalimide group can also be used. In the case where the chemically reactive functional group is a functional group which is protected by a protective group, it is necessary that the protective group is stable in the acidic conditions of the acetalization reaction and can be deprotected under reaction conditions other than catalytic reduction by which the benzylidene acetal group is decomposed. As to preferred combinations of the functional group to be protected and the protective group, when the functional group to be protected is an amino group, for example, an acyl protective group and a carbamate protective group are exemplified, and specific examples thereof include a trifluoroacetyl group, a 9-fluorenylmethyloxycarbonyl group and a 2-(trimethylsilyl)ethyloxycarbonyl group. When the functional group to be protected is a hydroxy group, for example, a silyl protective group and an acyl protective group are exemplified, and specific examples thereof include a tert-butyldiphenylsilyl group, a tert-butyldimethylsilyl group, a triisopropylsilyl group, an acetyl group and a pivaloyl group. When the functional group to be protected is a carboxy group, for example, an alkyl ester protective group and a silyl ester protective group are exemplified, and specific examples thereof include a methyl group, a 9-fluorenylmethyl group and a tert-butyldimethylsilyl group. When the functional group to be protected is a sulfanyl group, for example, a thioether protective group, a thiocarbonate protective group and a disulfide protective group are exemplified, and specific examples thereof include an S-2,4-dinitrophenyl group, an S-9-fluorenylmethyloxycarbonyl group and an S-tert-butyldisulfide group. The typical deprotection conditions of the protective group are described in the literature described above, and the reaction conditions suitable for each of the protective groups can be selected. However, in the case where the chemically reactive functional group is a functional group which does not inhibit the acetalization reaction even when it is not protected by a protective group, it is not necessary to use a protective group.

(B) Synthesis of Polyethylene Glycol Intermediate

Ethylene oxide is polymerized in an amount of 3 to 2,000 molar equivalents to pentaerythritol, which is an initiator, in toluene or with no solvent under alkaline conditions, for example, metallic sodium, metallic potassium, sodium hydride or potassium hydride to obtain polyethylene glycol of formula (6) shown below. As the initiator for use in the invention, a divalent to octavalent compound having a hydroxyl group or an amino group is preferably used. Specific examples of the compound having a hydroxyl group include an alcohol described below. Divalent alcohol includes ethylene glycol, diethylene glycol, propylene glycol, water, 1,4-butanediol, 1,5-pentanediol, 1,6-hexanediol, 1,4-benzenediol and the like, trivalent or higher polyhydric alcohol includes glycerol, trimethylolpropane, triethanolamine, pentaerythritol, diglycerol, N,N,N′,N′-tetrakis(2-hydroxypropyl)ethylenediamine, xylitol, triglycerol, dipentaerythritol, sorbitol, hexaglycerol and the like. Specific examples of the compound having an amino group include ammonia, methylamine, ethylamine, aniline, monoethanolamine, diethanolamine, ethylenediamine, toluylenediamine, diethylenetriamine and the like. Since the polyethylene glycol obtained has a hydroxyl group which is a chemically reactive functional group, it can be used as it is in the coupling reaction with the cyclic benzylidene acetal low molecular weight compound.

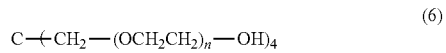

(6)

The polyethylene glycol of formula (6) is allowed to react with methanesulfonyl chloride in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, pyridine or 4-dimethylaminopyridine or an inorganic base, for example, sodium carbonate, sodium hydrogen carbonate, sodium acetate or potassium carbonate to obtain a polyethylene glycol intermediate of formula (7). The organic base and inorganic base may not be used. The use ratio of the organic base or the inorganic base is not particularly limited, and is preferably equimolar or more to the hydroxyl group of the polyethylene glycol of formula (6). Further, it is possible to use the organic base as a solvent. The compound obtained may be purified by a purification means, for example, extraction, recrystallization, adsorbent treatment, reprecipitation, column chromatography or supercritical extraction.

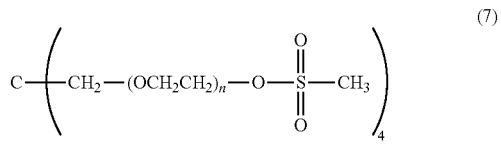

(7)

As the chemically reactive functional group in the polyethylene glycol intermediate of formula (7), other functional groups can also be used. Preferred examples of the chemically reactive functional group are functional groups wherein the bond generated by the coupling reaction between the polyethylene glycol intermediate and the cyclic benzylidene acetal low molecular weight compound described above becomes the ether bond, the ester bond, the carbonate bond, the urethane bond, the amide bond, the secondary amino group, the alkylene group containing any of these bonds and group, the single bond or the alkylene group contained in the divalent spacer $Z^1$ of formula (1), and specifically include, for example, a halogen atom, an active ester, an active carbonate, an aldehyde group, an amino group, a hydroxyl group and a carboxy group.

(C) Coupling Reaction Between Cyclic Benzylidene Acetal Low Molecular Weight Compound and Polyethylene Glycol Intermediate The benzylidene acetal low molecular weight compound of formula (5) and the polyethylene glycol intermediate of formula (7) are subjected to a coupling reaction in an aprotic solvent, for example, toluene, benzene, xylene, acetonitrile, ethyl acetate, diethyl ether, tert-butyl methyl ether, tetrahydrofuran, chloroform, dichloromethane, dimethyl sulfoxide, dimethylformamide or dimethylacetamide or with no solvent in the presence of an organic base, for example, triethylamine, N-methylmorpholine, potassium tert-butoxide or sodium hexamethyldisilazane or an inorganic base, for example, potassium carbonate, potassium hydroxide or sodium hydride to obtain a compound of formula (8). The use ratio of the organic base or the inorganic base is not particularly limited, and is preferably equimolar or more to the chemically reactive functional group of the polyethylene glycol intermediate of formula (7). Further, it is possible to use the organic base as a solvent. The compound obtained may be purified by the purification means described above.

obtained may be purified by the purification means described above.

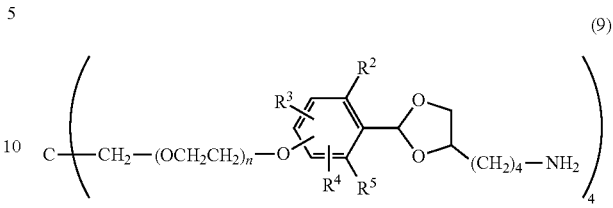

(9)

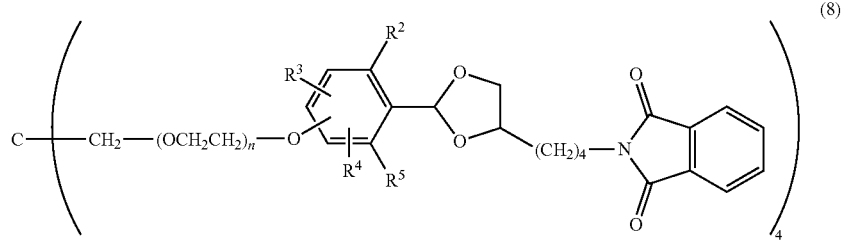

(8)

The chemically reactive functional group of the cyclic benzylidene acetal low molecular weight compound may be subjected to functional group conversion before the coupling reaction with the polyethylene glycol intermediate. The reaction conditions for the coupling reaction are determined depending on the combination of the chemically reactive functional group of the cyclic benzylidene acetal low molecular weight compound and the chemically reactive functional group of the polyethylene glycol intermediate and a conventionally known method can be used. However, it is necessary to appropriately select conditions which do not decompose the bonds contained in the cyclic benzylidene acetal group and the divalent spacers $Z^1$ and $Z^2$ described above of formula (1).

(D) Terminal Functional Group Conversion of the Polyethylene Glycol Derivative Having Cyclic Benzylidene Acetal Structure The compound of formula (8) is treated by using a basic organic compound, for example, ethylenediamine, methyl hydrazine or methylamine or a basic inorganic compound, for example, hydrazine, hydroxylamine or sodium hydroxide in a protic solvent, for example, water, methanol or ethanol, in an aprotic solvent, for example, acetonitrile, tetrahydrofuran, dimethyl sulfoxide, dimethylformamide or dimethylacetamide or with no solvent to obtain a compound of formula (9) in which the phthalimide group is deprotected and converted into an amino group. The use ratio of the basic compound is not particularly limited, and is preferably equimolar or more to the chemically reactive functional group of the compound of formula (8). Further, it is possible to use the basic compound as a solvent. The compound

EXAMPLES

The invention will be described more specifically with reference to the examples and comparative examples, but the invention should not be construed as being limited thereto.

In $^1$H-NMR analysis, JNM-ECP400 or JNM-ECA600 produced by JEOL DATUM Ltd. was used. For the measurement, a tube of 5 mm φ was used, and tetramethylsilane (TMS) was used as an internal standard substance in the case where a deuterated solvent was $CDCl_3$, $CD_3CN$ or $CD_3OD$, or HDO was used as a standard in the case of $D_2O$.

In gel permeation chromatography (GPC) analysis, there were used SHODEX GPC SYSTEM-11 as a GPC system, SHODEX RIX8 as a differential refractometer which was a detector, and three columns, i.e., SHODEX KF801L, KF803L and KF804L (φ8 mm×300 mm) connected in series as GPC columns, and the temperature of the column oven was set to 40° C. The measurement was performed using tetrahydrofuran as an eluent, at the flow rate of 1 mli/min, at the sample concentration of 0.1% by weight, and in the injection volume of 0.1 ml. The calibration curves prepared by using ethylene glycol, diethylene glycol and triethylene glycol produced by Kanto Chemical Co., Ltd. and Polymer Standards for GPC of polyethylene glycol or polyethylene oxide having a molecular weight of 600 to 70,000 produced by Polymer Laboratory Co., Ltd were used. For analysis of data, BORWIN GPC calculation program was used. Mn represents a number average molecular weight, Mw represents a weight average molecular weight, and polydispersity is indicated as a calculated value of Mw/Mn.

Synthesis Example 1

Into a 200 mL three-necked flask equipped with a thermometer, a nitrogen inlet tube, a stirrer, a Dean-stark tube and a condenser tube were charged 1,2,6-hexanetriol (30.0 g, 0.224 mol), acetone dimethyl acetal (25.6 g, 0.246 mol) and p-toluenesulfonic acid monohydrate (0.426 g, 2.24 mmol), and the reaction was performed at 80° C. for 3 hours while distilling off methanol. Triethylamine (0.453 g, 4.48 mmol) was added thereto and the mixture was stirred for a while, diluted with ethyl acetate, and washed with an aqueous 20% by weight sodium chloride solution. The organic layer was dried over anhydrous sodium sulfate, and after filtration, the solvent was distilled off under a reduced pressure. The residue was purified by silica gel column chromatography to obtain a compound of formula (10).

$^1$H-NMR (CDCl$_3$, internal standard TMS); δ (ppm):
1.35 (3H, s, —CH$_3$), 1.41 (3H, s, —CH$_3$), 1.49-1.67 (6H, m, >CHCH$_2$CH$_2$CH$_2$—), 2.07 (1H, brs, —OH), 3.51 (1H, t, —OCH$_2$CH<), 3.64 (2H, t, —CH$_2$OH), 4.04 (1H, dd, —OCH$_2$CH<), 4.07-4.10 (1H, m, —OCH$_2$CH<)

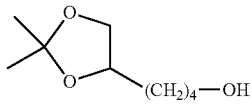

(10)

Synthesis Example 2

Into a 500 mL four-necked flask equipped with a thermometer, a nitrogen inlet tube, a stirrer and a condenser tube were charged the compound of formula (10) (20.0 g, 0.115 mol), triethylamine (23.3 g, 0.230 mol) and toluene (200 g) and the mixture was cooled to 10° C. or less. While continuing the cooling, methanesulfonyl chloride (19.8 g, 0.173 mol) prepared in a dropping funnel was gradually added dropwise thereto. After the completion of the dropwise addition, the reaction was performed at 20° C. for 2 hours. Ethanol (7.97 g, 0.173 mol) was added and the mixture was stirred for a while and filtered. The organic layer was washed with ion-exchanged water, dried over anhydrous sodium sulfate, and after filtration, the solvent was distilled off under a reduced pressure to obtain a compound of formula (11).

$^1$H-NMR (CDCl$_3$, internal standard TMS); δ (ppm):
1.35 (3H, s, —CH$_3$), 1.40 (3H, s, —CH$_3$), 1.44-1.83 (6H, m, >CHCH$_2$CH$_2$CH$_2$—), 3.01 (3H, s, —OSO$_2$CH$_3$, 3.51 (1H, t, —OCH$_2$CH<), 4.03-4.11 (2H, m, —OCH$_2$CH<, —OCH$_2$CH<), 4.24 (2H, t, —CHOSO$_2$CH$_3$)

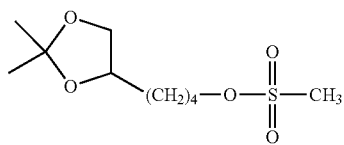

(11)

Synthesis Example 3

Into a 500 mL four-necked flask equipped with a thermometer, a nitrogen inlet tube, a stirrer and a condenser tube were charged the compound of formula (11) (20.0 g, 79.3 mmol), potassium phthalimide (17.6 g, 95.2 mmol) and dehydrated dimethylformamide (200 g), and the reaction was performed at 60° C. for 2 hours. The mixture was cooled to 10° C. or less, ion-exchanged water (400 g) was added thereto and after stirring for a while, the mixture was extracted with a mixed solution of ethyl acetate/hexane (60/40 in v/v). The organic layer was washed with an aqueous 0.2% by weight potassium carbonate solution and dried over anhydrous sodium sulfate. After filtration, the solvent was distilled off under a reduced pressure to obtain a compound of formula (12).

$^1$H-NMR (CDCl$_3$, internal standard TMS); δ (ppm):
1.34 (3H, s, —CH$_3$), 1.39 (3H, s, —CH$_3$), 1.44-1.75 (6H, m, >CHCH$_2$CH$_2$CH$_2$—), 3.50 (1H, t, —OCH$_2$CH<), 3.69 (2H, t, —CH$_2$L-phthalimide), 4.01-4.09 (2H, m, —OCH$_2$CH<, —OCH$_2$CH<), 7.71-7.85 (4H, m, -phthalimide)

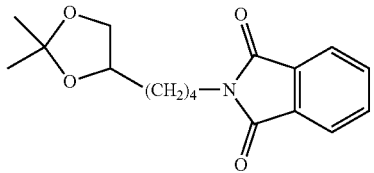

(12)

Synthesis Example 4

Into a 1 L four-necked flask equipped with a thermometer, a nitrogen inlet tube, a stirrer and a condenser tube were charged the compound of formula (12) (15.2 g, 50.0 mmol), p-toluenesulfonic acid monohydrate (951 mg, 5.00 mmol) and methanol (500 mL), and the reaction was performed at room temperature for 4 hours. Triethylamine (1.01 g, 10.0 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (13).

$^1$H-NMR (CD$_3$CN, internal standard TMS); δ (ppm):
1.24-1.61 (6H, m, >CHCH$_2$CH$_2$CH$_2$—), 2.69 (1H, t, —OH), 2.75 (1H, d, —OH), 3.17-3.21 (1H, m, —OCH$_2$CH<), 3.31-3.37 (1H, m, —OCH$_2$CH<), 3.39-3.43 (1H, m, —OCH$_2$CH<), 3.54 (2H, t, —CH$_2$-phthalimide), 7.67-7.75 (4H, m, -phthalimide)

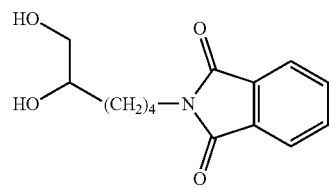

(13)

Synthesis Example 5

Into a 300 mL three-necked flask equipped with a thermometer, a nitrogen inlet tube, a stirrer, a Dean-stark tube and a condenser tube were charged the compound of formula (13) (3.87 g, 14.7 mmol), 4-hydroxybenzaldehyde (1.20 g, 9.83 mmol), p-toluenesulfonic acid monohydrate (187 mg, 0.983 mmol) and cyclopentyl methyl ether (180 g), and the reaction was performed for 4 hours while removing by-produced water by azeotropic distillation with cyclopentyl methyl ether. Triethylamine (199 mg, 1.97 mmol) was added thereto and after stirring for a while, the solvent was distilled off under a reduced pressure. The residue was dissolved in chloroform, the solution was washed with ion-exchanged water, and the organic layer was dried over anhydrous sodium sulfate. After filtration, the solvent was distilled off under a reduced pressure to obtain a compound of formula (14).

$^1$H-NMR (CDCl$_3$, internal standard TMS); δ (ppm):
1.41-1.80 (6H, m, >CHC$\underline{H}_2$C$\underline{H}_2$C$\underline{H}_2$—), 3.57-4.26 (5H, m, —OC$\underline{H}_2$CH<, —C$\underline{H}_2$-phthalimide), 5.71 (0.6H, s, >C$\underline{H}$—), 5.82 (0.4H, s, >C$\underline{H}$—), 6.79-6.82 (2H, m, arom.$\underline{H}$), 7.31-7.35 (2H, m, arom.$\underline{H}$), 7.70-7.86 (4H, m, -phthalimide)

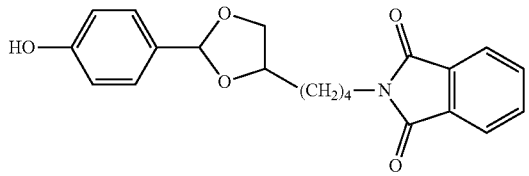

(14)

Synthesis Example 6

Into a 5 L autoclave were charged pentaerythritol (27.2 g, 0.200 mol), dehydrated toluene (400 g) and sodium methoxide (3.52 g, 0.065 mol), after the inside of the system was substituted with nitrogen, temperature was raised to 100° C., followed by stirring for 30 minutes. Then, water and methanol were removed by azeotropic distillation with toluene. After adding ethylene oxide (1.97 kg, 44.8 mol) at 100 to 130° C. under a pressure of 1 MPa or less, the reaction was further continued for 2 hours. After the unreacted ethylene oxide gas was removed under a reduced pressure, the mixture was cooled to 60° C. and pH was adjusted to 7.5 with an aqueous 85% phosphoric acid solution to obtain a compound of formula (15).

$^1$H-NMR (CDCl$_3$, internal standard TMS); δ (ppm):
2.76 (4H, t, O$\underline{H}$), 3.41-3.83 (920H, m, —C$\underline{H}_2$—(OC$\underline{H}_2$C$\underline{H}_2$)$_n$—)

GPC analysis; number average molecular weight (Mn): 9170, weight average molecular weight (Mw): 9298, polydispersity (Mw/Mn): 1.014

(15)

n = about 57

Synthesis Example 7

Into a 500 mL three-necked flask equipped with a thermometer, a nitrogen inlet tube, a stirrer, a Dean-stark tube and a condenser tube were charged the compound of formula (15) (100 g, 10.0 mmol) and toluene (250 g), and water was removed by azeotropic distillation with toluene. After cooling to 40° C., triethylamine (6.07 g, 60.0 mmol) was charged and methanesulfonyl chloride (5.04 g, 44.0 mmol) prepared in a dropping funnel was gradually added dropwise thereto. After the completion of the dropwise addition, the reaction was performed at 40° C. for 3 hours. Ethanol (2.03 g, 44.0 mmol) was added thereto and the mixture was stirred for a while, filtered, and diluted with ethyl acetate (300 g). Crystallization was performed by adding hexane (500 g), and after filtration, the crystals were dissolved in ethyl acetate (500 g). Crystallization was again performed by adding hexane (400 g), and after filtration, the crystals were dried under a reduced pressure to obtain a compound of formula (16).

$^1$H-NMR (CDCl$_3$, internal standard TMS); δ (ppm):
3.08 (12H, s, —OSO$_2$C$\underline{H}_3$), 3.47-3.85 (912H, m, —C$\underline{H}_2$—(OC$\underline{H}_2$C$\underline{H}_2$)$_n$—OC$\underline{H}_2$—), 4.37-4.39 (8H, m, —C$\underline{H}_2$OSO$_2$CH$_3$)

GPC analysis; number average molecular weight (Mn): 9496, weight average molecular weight (Mw): 9632, polydispersity (Mw/Mn): 1.014

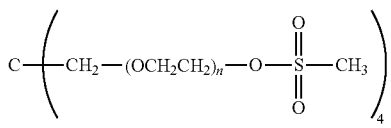

(16)

n = about 57

Synthesis Example 8

Into a 100 mL three-necked flask equipped with a thermometer, a nitrogen inlet tube, a stirrer and a condenser tube were charged the compound of formula (16) (5.00 g, 0.500 mmol), the compound of formula (14) (1.10 g, 3.00 mmol), potassium carbonate (1.38 g, 10.0 mmol) and acetonitrile (25 g), and the reaction was performed at 80° C. for 4 hours. After distilled off the solvent under a reduced pressure, the residue was dissolved in ethyl acetate (100 g) and the solution was filtered. Crystallization was performed by adding hexane (100 g), and after filtration, the crystals were dried under a reduced pressure to obtain a compound of formula (17).

$^1$H-NMR (CDCl$_3$, internal standard TMS); δ (ppm):
1.39-1.81 (24H, m, >CHC$\underline{H}_2$C$\underline{H}_2$C$\underline{H}_2$—), 3.41-4.23 (940H, m, —C$\underline{H}_2$—(OC$\underline{H}_2$C$\underline{H}_2$)$_n$—, —OC$\underline{H}_2$CH<, —C$\underline{H}_2$-phthalimide), 5.72 (2.4H, s, >C$\underline{H}$—), 5.84 (1.6H, s, >C$\underline{H}$—), 6.89-6.91 (8H, m, arom.$\underline{H}$), 7.36-7.38 (8H, m, arom.$\underline{H}$), 7.71-7.85 (16H, m, -phthalimide)

GPC analysis: number average molecular weight (Mn): 10557, weight average molecular weight (Mw): 10736, polydispersity (Mw/Mn): 1.017

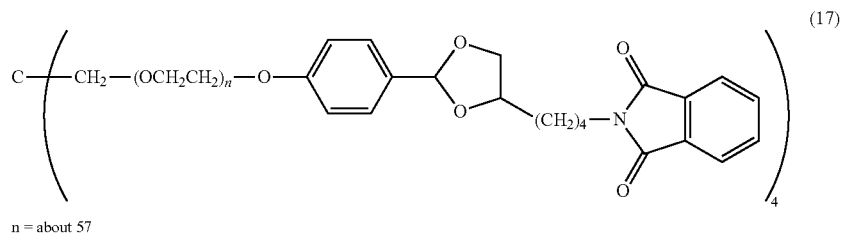

(17)

n = about 57

Synthesis Example 9

Into a 50 mL three-necked flask equipped with a thermometer, a nitrogen inlet tube, a stirrer and a condenser tube were charged the compound of formula (17) (4.00 g, 0.400 mmol), methanol (14 g) and ethylene diamine monohydrate (0.781 g, 10.0 mmol), and the reaction was performed at 40° C. for 4 hours. The mixture was diluted with an aqueous 20% by weight sodium chloride solution, extracted with dichloromethane, and then the solvent was distilled off under a reduced pressure. The residue was dissolved in ethyl acetate (50 g), dried over anhydrous sodium sulfate, filtered, and crystallized by adding hexane (50 g). After filtration, the crystals were dried under a reduced pressure to obtain a compound of formula (18).

$^1$H-NMR (CDCl$_3$, internal standard TMS); δ (ppm):
1.39-1.81 (24H, m, >CHC$\underline{H}_2$C$\underline{H}_2$C$\underline{H}_2$—), 2.71 (8H, t, —C$\underline{H}_2$—NH$_2$), 3.41-4.23 (932H, m, —C$\underline{H}_2$—(OC$\underline{H}_2$C$\underline{H}_2$)$_n$—, —OC$\underline{H}_2$C$\underline{H}$<), 5.74 (2.4H, s, >C$\underline{H}$—), 5.85 (1.6H, s, >C$\underline{H}$—), 6.90-6.92 (8H, m. arom.$\underline{H}$), 7.37-7.40 (8H, m, arom.$\underline{H}$)

GPC analysis; number average molecular weight (Mn): 10037, weight average molecular weight (Mw): 10225, polydispersity (Mw/Mn): 1.019

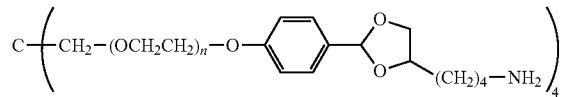

(18)

n = about 57

Synthesis Example 10

A compound of formula (19) was obtained in the same manner as in Synthesis Examples 1 to 5, 8 and 9 using 3-fluoro-4-hydroxybenzaldehyde and the compound of formula (16).

$^1$H-NMR (CDCl$_3$, internal standard TMS); δ (ppm):
1.39-1.81 (24H, m, >CHC$\underline{H}_2$C$\underline{H}_2$C$\underline{H}_2$—), 2.71 (8H, s, —C$\underline{H}_2$—NH$_2$), 3.41-4.23 (932H, m, —C$\underline{H}_2$—(OC$\underline{H}_2$C$\underline{H}_2$)$_n$—, —OC$\underline{H}_2$C$\underline{H}$<), 5.74 (2.4H, s, >C$\underline{H}$—), 5.85 (1.6H, s, >C$\underline{H}$—), 6.95-7.25 (12H, m, arom.$\underline{H}$)

GPC analysis; number average molecular weight (Mn): 10107, weight average molecular weight (Mw): 10298, polydispersity (Mw/Mn): 1.019

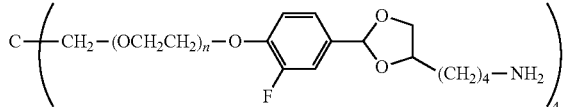

(19)

n = about 57

Synthesis Example 11

A compound of formula (20) was obtained in the same manner as in Synthesis Examples 1 to 5, 8 and 9 using 3-hydroxybenzaldehyde and the compound of formula (16).

$^1$H-NMR (CDCl$_3$, internal standard TMS); δ (ppm):
1.39-1.81 (24H, m, >CHC$\underline{H}_2$C$\underline{H}_2$C$\underline{H}_2$), 2.71 (8H, t, —C$\underline{H}_2$—NH$_2$), 3.41-423 (932H, m, —C$\underline{H}_2$—(OC$\underline{H}_2$C$\underline{H}_2$)$_n$—, —OC$\underline{H}_2$C$\underline{H}$<), 5.74 (2.4H, s, >C$\underline{H}$—), 5.85 (1.6H, s, >C$\underline{H}$—), 6.89-7.27 (16H, m, arom.$\underline{H}$)

GPC analysis: number average molecular weight (Mn): 10037, weight average molecular weight (Mw): 10225, polydispersity (Mw/Mn): 1.019

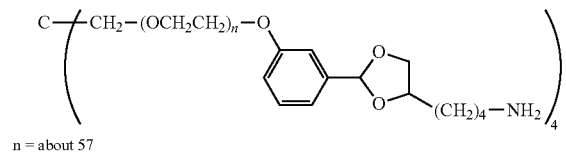

(20)

n = about 57

Synthesis Example 12

Into a 300 mL three-necked flask equipped with a thermometer, a nitrogen inlet tube, a stirrer, a Dean-stark tube and a condenser tube were charged 1,2,6-hexanetriol (2.01 g, 15.0 mmol), 3-hydroxybenzaldehyde (1.22 g, 10.0 mmol), p-toluenesulfonic acid monohydrate (19.0 mg, 0.100 mmol) and cyclopentyl methyl ether (61 g), and the reaction was performed for 4 hours while removing by-produced water by azeotropic distillation with cyclopentyl methyl ether. Triethylamine (50.6 mg, 0.500 mmol) was added thereto and after stirring for a while, the mixture was washed with ion-exchanged water, and the organic layer was dried over anhydrous sodium sulfate. After filtration, the solvent was distilled off under a reduced pressure to obtain a compound of formula (21).

$^1$H-NMR (CDCl$_3$, internal standard TMS); δ (ppm):
1.42-1.80 (6H, m, >CHC$\underline{H}_2$C$\underline{H}_2$C$\underline{H}_2$—), 3.61-4.24 (5H, m, —OC$\underline{H}_2$C$\underline{H}$<, —C$\underline{H}_2$—OH), 5.78 (0.6H, s, >C$\underline{H}$—), 5.89 (0.4H, s, >C$\underline{H}$—), 6.83-7.26 (4H, m, arom.$\underline{H}$)

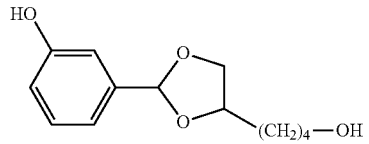

(21)

Synthesis Example 13

Into a 100 mL three-necked flask equipped with a thermometer, a nitrogen inlet tube, a stirrer and a condenser tube were charged the compound of formula (16) (5.00 g, 0.500 mmol), the compound of formula (21) (572 mg, 2.40 mmol), potassium carbonate (1.38 g, 10.0 mmol) and acetonitrile (25 g), and the reaction was performed at 80° C. for 4 hours. After distilled off the solvent under a reduced pressure, the residue was dissolved in ethyl acetate (100 g) and the solution was filtered. Crystallization was performed by adding hexane (100 g), and after filtration, the crystals were dried under a reduced pressure to obtain a compound of formula (22).

¹H-NMR (CDCl₃, internal standard TMS); δ (ppm):
1.39-1.81 (24H, m, >CHC$\underline{H}_2$C$\underline{H}_2$C$\underline{H}_2$—), 3.41-4.23 (940H, m, —C$\underline{H}_2$—(OC$\underline{H}_2$C$\underline{H}_2$)$_n$—, —OC$\underline{H}_2$C$\underline{H}$<, —C$\underline{H}_2$—OH), 5.77 (2.4H, s, >C$\underline{H}$—), 5.90 (1.6H, s, >C$\underline{H}$—), 6.89-7.26 (16H, m, arom.$\underline{H}$)

GPC analysis; number average molecular weight (Mn): 10065, weight average molecular weight (Mw): 10236, polydispersity (Mw/Mn): 1.017

(22)

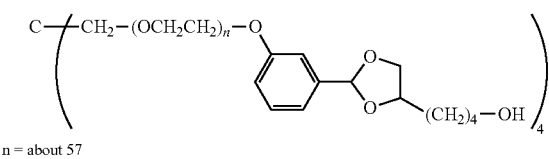

n = about 57

Synthesis Example 14

A compound of formula (23) was obtained by allowing to react the compound of formula (22) with N,N'-disuccinimidyl carbonate in dichloromethane in the presence of triethylamine.

¹H-NMR (CDCl₃, internal standard TMS); δ (ppm):
1.39-1.87 (24H, m, >CHC$\underline{H}_2$C$\underline{H}_2$C$\underline{H}_2$—), 2.84 (16H, s, -succinimid), 3.41-4.23 (940H, m, —C$\underline{H}_2$—(OC$\underline{H}_2$C$\underline{H}_2$)$_n$—, —OC$\underline{H}_2$C$\underline{H}$<, —C$\underline{H}_2$O—COO-succinimide), 5.77 (2.4H, s, >C$\underline{H}$—), 5.89 (1.6H, s, >C$\underline{H}$—), 6.89-7.26 (16H, m, arom.$\underline{H}$)

GPC analysis: number average molecular weight (Mn): 10629, weight average molecular weight (Mw): 10820, polydispersity (Mw/Mn): 1.018

(23)

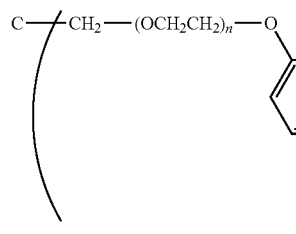

n = about 57

Synthesis of Polyethylene Glycol Crosslinking Agent

Synthesis Example 15

Into a 200 mL three-necked flask equipped with a thermometer, a nitrogen inlet tube and a stirrer were charged the compound of formula (15) (5.00 g, 0.500 mmol), potassium hydroxide (10.0 g) and toluene (75.0 g), and under a nitrogen atmosphere ethyl 6-bromohexanoate (8.92 g, 40.0 mmol) was dropwise added with stirring at 40° C. over 2 hours. After the completion of the dropwise addition, the mixture was allowed to react for 5 hours. After addition of ion-exchanged water, hydrolysis was performed at 70° C. for 2 hours. The reaction solution was cooled, concentrated hydrochloric acid (7.0 g) was dropwise added thereto with stirring and allowed to stand, and then the organic layer was removed. After washing the aqueous layer with ethyl acetate, the aqueous layer was extracted with chloroform, and the organic layer was dried over anhydrous magnesium sulfate. After filtration, the solvent was distilled off under a reduced pressure. The residue was dissolved in ethyl acetate (35 g), crystallization was performed by adding hexane (10 g), and after filtration, the crystals were dried under a reduced pressure to obtain a compound of formula (24).

¹H-NMR (CDCl₃, internal standard TMS); δ (ppm):
1.39-1.44 (8H, m, —OCH₂CH₂C$\underline{H}_2$CH₂CH₂C(O)O—), 1.58-1.68 (16H, m, —OCH₂C$\underline{H}_2$CH₂C$\underline{H}_2$CH₂C(O)O—), 2.34 (8H, t, —OCH₂CH₂CH₂CH₂C$\underline{H}_2$C(O)O—), 3.41-3.77 (928H, m, —C$\underline{H}_2$—(OC$\underline{H}_2$C$\underline{H}_2$)$_n$—, —OC$\underline{H}_2$CH₂CH₂CH₂CH₂C(O)O—)

(24)

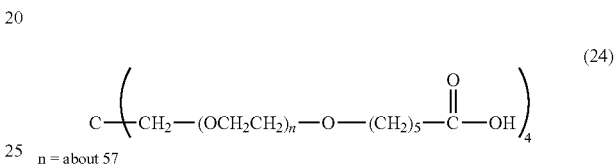

n = about 57

Synthesis Example 16

Into a 50 mL three-necked flask equipped with a thermometer, a nitrogen inlet tube and a stirrer were charged the compound of formula (24) (2.00 g, 0.200 mmol) and toluene (6 g) to be dissolved, then N-hydroxysuccinimide (48.3 mg, 0.420 mmol) and 1,3-dicyclohexylcarbodiimide (82.5 mg, 0.400 mmol) were charged, the reaction was performed at 40° C. for 2 hours. After filtration of the reaction solution, hexane was added to the filtrate to perform crystallization. After filtration, the crystals were dried under a reduced pressure to obtain a compound of formula (25).

¹H-NMR (CDCl₃, internal standard TMS); δ (ppm):
1.43-1.49 (8H, m, —OCH₂CH₂C$\underline{H}_2$CH₂CH₂C(O)O—), 1.59-1.66 (8H, m, —OCH₂CH₂CH₂C$\underline{H}_2$CH₂C(O)O—), 1.73-1.81 (8H, m, —OCH₂C$\underline{H}_2$CH₂C$\underline{H}_2$CH₂C(O)O—), 2.61 (8H, m, —OCH₂CH₂CH₂CH₂C$\underline{H}_2$C(O)O—), 2.84 (16H, s, -succinimide), 3.41-3.83 (928H, m, —C$\underline{H}_2$—(OC$\underline{H}_2$C$\underline{H}_2$O)$_n$—, —OC$\underline{H}_2$CH₂CH₂CH₂CH₂C(O)O—)

GPC analysis; number average molecular weight (Mn): 8987, weight average molecular weight (Mw): 9229, polydispersity (Mw/Mn): 1.027

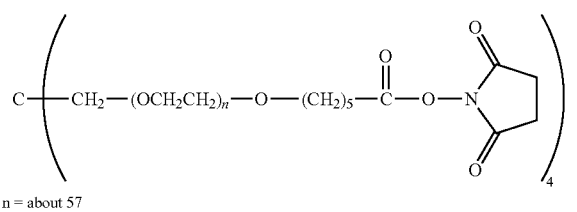

(25)

n = about 57

Synthesis Example 17

Into a 50 mL three-necked flask equipped with a thermometer, a nitrogen inlet tube, a stirrer and a condenser tube were charged the compound of formula (15) (10.0 g, 1.00 mmol) and ion-exchange water (10.0 g) to be dissolved by heating, then an aqueous 48% potassium hydroxide solution (626 mg) was added thereto at 10° C. or less. Subsequently, acrylonitrile (5.30 g, 100 mmol) was dropwise added at 5 to 10° C. After the completion of the dropwise addition, the mixture was allowed to react for 4 hours, and after adding ion-exchanged water (10 g), an aqueous 85% phosphoric acid solution (6.00 g) was added dropwise to neutralize. After washing the aqueous layer with ethyl acetate, the aqueous layer was extracted with chloroform (45 g), and the organic layer was dried over anhydrous magnesium sulfate. After filtration, the solvent was distilled off under a reduced pressure. The residue was dissolved in ethyl acetate (35 g), crystallization was performed by adding hexane (40 g), and after filtration, the crystals were dried under a reduced pressure to obtain a compound of formula (26).

$^1$H-NMR (CDCl$_3$, internal standard TMS); δ (ppm): 2.63 (8H, t, —OCH$_2$C$\underline{H}_2$CN), 3.41-3.82 (928H, m, —C$\underline{H}_2$—(OC$\underline{H}_2$C$\underline{H}_2$)$_n$—, —OC$\underline{H}_2$CH$_2$CN)

GPC analysis; number average molecular weight (Mn): 9315, weight average molecular weight (Mw): 9537, polydispersity (Mw/Mn): 1.024

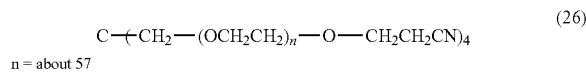

(26)

n = about 57

Synthesis Example 18

To a 1 L autoclave were added the compound of formula (26) (2.00 g, 0.200 mmol), toluene (560 g) and stabilized nickel catalyst (Ni-5136p produced by N.E. Chemcat Corp, 0.12 g) and the temperature was raised to 60° C. The pressure was raised with ammonia until the internal pressure reached to 1 MPa and then, the pressure was raised with hydrogen until the internal pressure reached to 4.5 MPa, followed by reacting at 130° C. for 3 hours. After the reaction, the reaction solution was cooled to 80° C. and purging with nitrogen was repeated. The whole amount of the reaction solution was taken out, filtered, and then crystallization was performed by adding hexane. After filtration, the crystals were dried under a reduced pressure to obtain a compound of formula (27).

$^1$H-NMR (CDCl$_3$, internal standard TMS); δ (ppm): 1.73 (8H, quint, —OCH$_2$C$\underline{H}_2$CH$_2$NH$_2$), 2.79 (8H, t, —OCH$_2$CH$_2$C$\underline{H}_2$NH$_2$), 3.41-3.77 (928H, m, —C$\underline{H}_2$—(OC$\underline{H}_2$CH$_2$)$_n$—, —OC$\underline{H}_2$CH$_2$CH$_2$NH$_2$)

GPC analysis; number average molecular weight (Mn): 8903, weight average molecular weight (Mw): 9100, polydispersity (Mw/Mn): 1.022

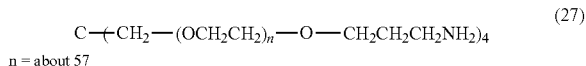

(27)

n = about 57

<Degradation Test of Hydrogel Using Polyethylene Glycol Crosslinking Agent>

The decomposition behavior of the hydrogel of the invention was investigated. A hydrogel was prepared by mixing a fluorescent labeled polyethylene glycol derivative, soaked in a buffer to decompose, and the solution in which the hydrogel had been soaked was collected at an arbitrary time. The fluorescence intensity of the solution containing the fluorescent labeled polyethylene glycol derivative was measured and the residual ratio of the hydrogel at the arbitrary time was determined.

Synthesis Example 19

Into a 50 mL three-necked flask equipped with a thermometer, a nitrogen inlet tube, a stirrer and a condenser tube were charged the compound of formula (27) (0.470 g, 0.047 mmol) and dichloromethane (5.70 g), 5(6)-carboxytetramethyl-rhodamine succinimidyl ester (25.0 mg 0.047 mmol) was added thereto, and the reaction was performed at 25° C. for 2 hours. The reaction solution was diluted with dichloromethane (44.6 g), washed with ion-exchanged water, and then the solvent was distilled off under a reduced pressure. The residue was dissolved in ethyl acetate, and dried over anhydrous sodium sulfate. After filtration, crystallization was performed by adding hexane. After filtration, the crystals were dried under a reduced pressure to obtain a fluorescent labeled compound (28). The labeling index for the amino group of the compound (28) measured by $^1$H-NMR was 18%.

(i) Production of Hydrogel

Example 1

The compound of formula (18) (29.5 mg) and the compound (28) of Synthesis Example 19 (0.5 mg) were dissolved in phosphate buffer of pH 7.4 (20 mM, 1 mL). The compound of formula (25) (30.0 mg) of the crosslinking agent was dissolved in phosphate buffer of pH 7.4 (20 mM, 1 mL). The two solutions described above were filled into a syringe (dual syringe) which can extrude simultaneously each of two kinds of solutions to mix at the tip, poured into a polyterrafluoroethylene cylindrical mold (inner diameter of 6.0 mm, height of 3.2 mm), and allowed to stand at room temperature for 30 minutes to obtain Hydrogel (29).

(ii) Degradation Test of Hydrogel (Test 1)

Hydrogel (29) produced in Example 1 was put into a 48-well plate (color: clear, bottom shape: flat bottom) produced by Iwaki & Co., Ltd. and soaked in citrate buffer of pH 5.0 (100 mM, 0.5 mL). After shielding the well plate, the well plate was shaken by using a shaker (SHAKER RS-2 produced by Iuchi Co., Ltd.) at speed of 100 rpm in a constant temperature chamber (SLI-700 produced by Tokyo Rikakikai Co. Ltd.) of 37° C. to initiate the degradation test. The solution in which the hydrogel had been soaked was collected at an arbitrary time, and new citrate buffer of pH 5.0 (100 mM, 0.5 mL) was promptly added. The collection of the solution and the addition of the buffer were repeated. The fluorescence intensity of the solution collected was measured and the residual ratio of the hydrogel was calculated. Using citrate buffer of pH 5.5 (100 mM), phosphate buffers of pH 6.0 and pH 7.4 (100 mM), the degradation tests were performed in the same manner.

For the measurement of fluorescence intensity, SPECTRA Max M3 produced by Molecular Devices Inc. was used. For the measurement, a 384-well plate (color: black, bottom shape: flat bottom) produced by Corning Inc. was used. The measurement conditions were set as follows: excitation wavelength of 555 nm, detection wavelength of 580 nm, PMT (Photomultiplier tube) Gain (photomultiplier tube sensitivity) of 350, and the number of times of excitation light irradiation of 6 times. 100 µL of each solution collected in Test 1 was put into the well plate and the fluorescence intensity thereof was measured. From the fluorescence intensity was calculated the residual ratio of the hydrogel using a calibration curve. The calibration curve was prepared by dissolving the compound (28) in a buffer to prepare a solution of 02 mg/mL, and diluting stepwise with the buffer to prepare 8 kinds of standard solutions having different concentrations.

Example 2

A hydrogel was produced in the same manner as in Example 1 using the compound of formula (19), and using the resulting hydrogel (30) the degradation test was performed in the same manner as in Test 1.

Example 3

A hydrogel was produced in the same manner as in Example 1 using the compound of formula (20), and using the resulting hydrogel (31) the degradation test was performed in the same manner as in Test 1.

Comparative Example 1

A hydrogel was produced in the same manner as in Example 1 using the compound of formula (27), and using the resulting hydrogel (32) the degradation test was performed in the same manner as in Test 1.

Degradation Test of Hydrogel Using Polypeptide Crosslinking Agent

Synthesis Example 20

Into a 50 mL three-necked flask equipped with a thermometer, a nitrogen inlet tube, a stirrer and a condenser tube were charged the compound of formula (23) (0.500 g, 0.050 mmol) and dichloromethane (6.0 g), 5-TAMRA-PEO3-amine (41.6 mg, 0.050 mmol) was added thereto, and the reaction was performed at 25° C. for 2 hours. The reaction solution was diluted with dichloromethane (47.5 g), washed with ion-exchanged water, and then the solvent was distilled off under a reduced pressure. The residue was dissolved in ethyl acetate, and dried over anhydrous sodium sulfate. After filtration, crystallization was performed by adding hexane. After filtration, the crystals were dried under a reduced pressure to obtain a fluorescent labeled compound (33). The labeling index for the succinimidyl group of the compound (33) measured by $^1$H-NMR was 17%.

(i) Production of Hydrogel

Example 4

The compound (23) (59.5 mg) and the compound (33) of Synthesis Example 20 (0.5 mg) were dissolved in phosphate buffer of pH 7.4 (20 mM, 1 mL). Trilysine (2.4 mg, produced by Sigma-Aldrich Corp.) of the crosslinking agent was dissolved in phosphate buffer of pH 9.0 (20 mM, 1 mL). The two solutions described above were filled into a syringe (dual syringe) which can extrude simultaneously each of two kinds of solutions to mix at the tip, poured into a polytetrafluoroethylene cylindrical mold (inner diameter of 6.0 mm, height of 3.2 mm), and allowed to stand at room temperature for 30 minutes to obtain Hydrogel (34).

(ii) Degradation Test of Hydrogel

Example 5

Using Hydrogel (34) thus-obtained, the degradation test was performed in the same manner as in Test 1.

Figure 4:
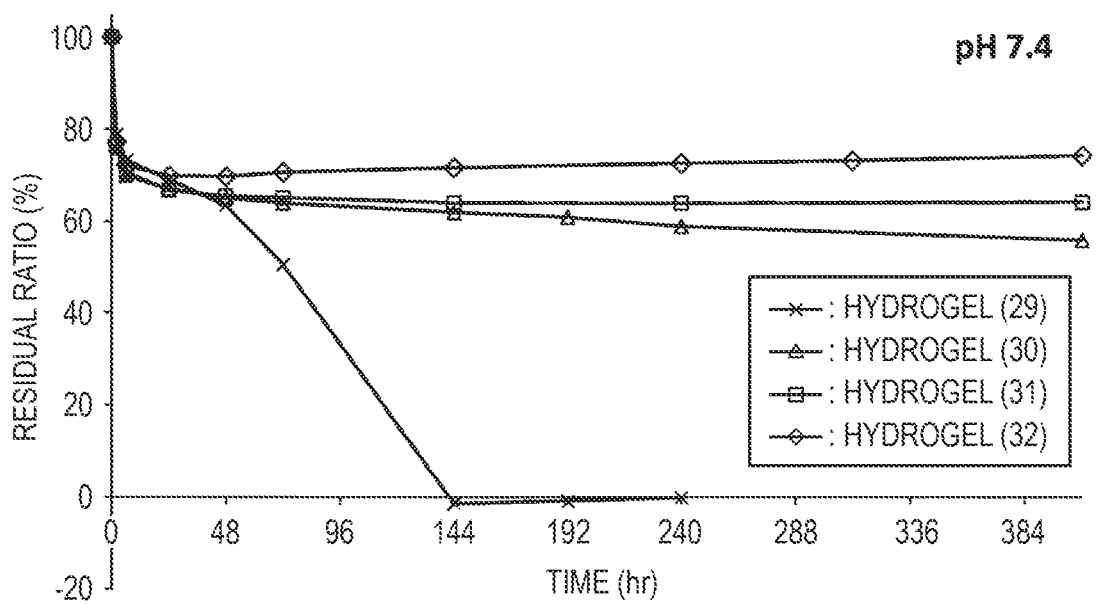
FIG. 4 shows results of the degradation test with hydrogels (29), (30), (31) and (32) each formed by using the compounds of formula (18), formula (19) and formula (20) described in Examples and the compound of formula (27) described in Comparative Examples performed in phosphate buffer of pH 7.4 at 37° C.
Figure 5:
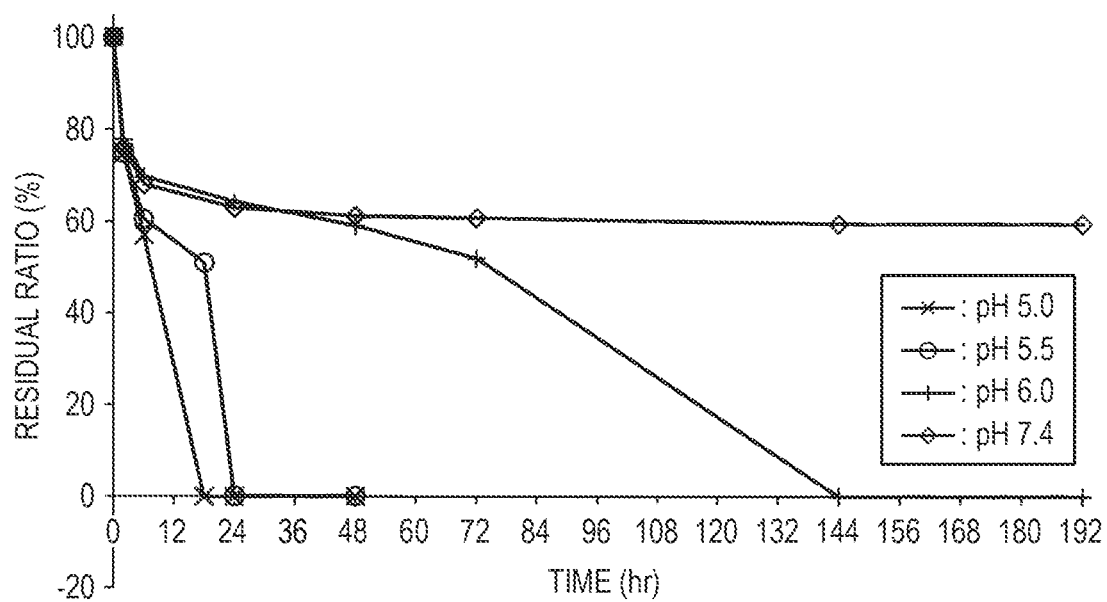
FIG. 5 shows results of the degradation test with Hydrogel (34) formed by using Compound (23) described in Examples and trilysine performed in citrate buffers of pH 5.0 and 5.5 and phosphate buffers of pH 6.0 and 7.4 at 37° C.

As shown in FIG. 1 to FIG. 5, the degradation rates of the hydrogels having a cyclic benzylidene acetal structure of the invention had a high correlation to the hydrolysis rates of the cyclic benzylidene acetals in the polyethylene glycol derivatives having a cyclic benzylidene acetal structure constituting the respective hydrogels. Therefore, it was shown that the hydrogel of the invention can control the degradation rate by appropriately selecting the kind and position of the substituent(s) on the benzene ring of the cyclic benzylidene acetal without changing the crosslink density. Further, as shown in FIG. 4, it was confirmed that Hydrogel (29) gradually degraded even at pH 7.4. On the other hand, Hydrogel (32) did not disappear even after 30 days.

<Release Behavior of Model Drug Encapsulated in Hydrogel>

In order to investigate the release behavior of a drug encapsulated in the hydrogel of the invention, a hydrogel in which fluorescein isothiocyanate-dextran (FITC-Dextran) was encapsulated as a model drug was prepared, and soaked in a buffer to decompose. The solution in which the hydrogel had been soaked was collected at an arbitrary time, and the fluorescence intensity of the solution containing FITC-Dextran was measured to determine the release ratio.

(i) Production of Hydrogel Encapsulating Model Drug

Example 6

The compound of formula (18) (200 mg) and FITC-Dextran (produced by Sigma-Aldrich Corp., molecular weight: 70,000, 2.5 mg) were dissolved in phosphate buffer of pH 7.4 (20 mM, 1 mL). The compound of formula (25) (200 mg) of the crosslinking agent was dissolved in phosphate buffer of pH 7.4 (20 mM, 1 mL). The respective solutions were filled into a dual syringe, poured into a polytetrafluoroethylene cylindrical mold (inner diameter of 6.0 mm, height of 3.2 mm) while mixing the two solutions, and allowed to stand at room temperature for 30 minutes to obtain Hydrogel (35).

(ii) Release Test of Model Drug (Test 2)

Hydrogel (35) produced in Example 6 was put into a 48-well plate (color: clear, bottom shape: flat bottom) produced by Iwaki & Co., Ltd. and soaked in citrate buffer of pH 5.5 (200 mM, 0.5 mL). After shielding the well plate, the well plate was shaken by using a shaker (SHAKER RS-2 produced by Iuchi Co., Ltd.) at speed of 100 rpm in a constant temperature chamber (SLI-700 produced by Tokyo Rikakikai Co. Ltd.) of 37° C. to initiate the release test. The solution in which the hydrogel had been soaked was collected at an arbitrary time, and new citrate buffer of pH 5.5 (200 mM, 0.5 mL) was promptly added. The collection of the solution and the addition of the buffer were repeated at an arbitrary time. Then, the fluorescence intensity of the solution collected was measured and the release ratio was calculated. By changing the buffer described above to phosphate buffers of pH 6.5, pH 7.0, pH 7.4 and pH 8.0 (200 mM), the tests were performed in the same manner.

For the measurement of fluorescence intensity, SPECTRA Max M3 produced by Molecular Devices Inc. was used. For the measurement, a 384-well plate (color: black, bottom shape: flat bottom) produced by Corning Inc. was used. The measurement conditions were set as follows: excitation wavelength of 494 nm, detection wavelength of 518 nm, PMT (Photomultiplier tube) Gain (photomultiplier tube sensitivity) of 300, and the number of times of excitation light irradiation of 6 times. 100 μL of each solution collected in Example 7 was put into the well plate and the fluorescence intensity thereof was measured. From the fluorescence intensity was calculated the release ratio using a calibration curve. The calibration curve was prepared by dissolving FITC-Dextran in a buffer to prepare a solution of 0.2 mg/mL, and diluting stepwise with the buffer to prepare 8 kinds of standard solutions having different concentrations.

Example 7

A hydrogel was produced in the same manner as in Example 6 using the compound of formula (20), and using the resulting hydrogel (36) the release test was performed in the same manner as in Test 2. As buffer for soaking the hydrogel, citrate buffers of pH 5.0 and pH 5.5 (200 mM) and phosphate buffers of pH 6.0 and pH 7.4 (200 mM) were used, respectively.

Comparative Example 2

A hydrogel was produced in the same manner as in Example 6 using the compound of formula (27), and using the resulting hydrogel (37) the release test was performed in the same manner as in Test 2. As buffer for soaking the hydrogel, citrate buffer of pH 5.0 (200 mM) was used.

Figure 6:
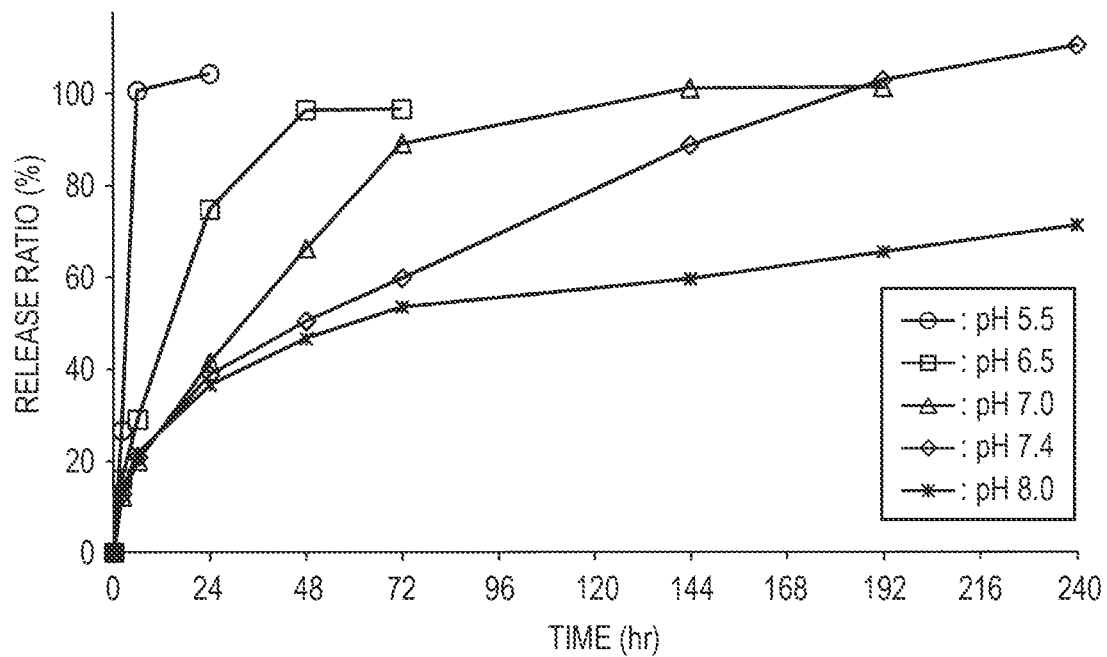
FIG. 6 shows results of the FITC-Dextran release test with Hydrogel (35) formed by encapsulating fluorescein isothiocyanate-dextran (FITC-Dextran), as a model drug, into the compound of formula (18) described in Examples performed in citrate buffer of pH 5.5 and phosphate buffers of pH 6.5, 7.0, 7.4 and 8.0 at 37° C.

As shown in FIG. 6, Hydrogel (35) released the model drug encapsulated at different rates corresponding to each pH. The release rate of the model drug had a high correlation to the hydrolysis rate of the cyclic benzylidene acetal in the polyethylene glycol derivative having a cyclic benzylidene acetal structure constituting Hydrogel (35). Therefore, it was shown that the hydrogel of the invention can control the release rate of the drug encapsulated by appropriately selecting the kind and position of the substituent(s) on the benzene ring of the cyclic benzylidene acetal without changing the crosslink density.

Figure 7:
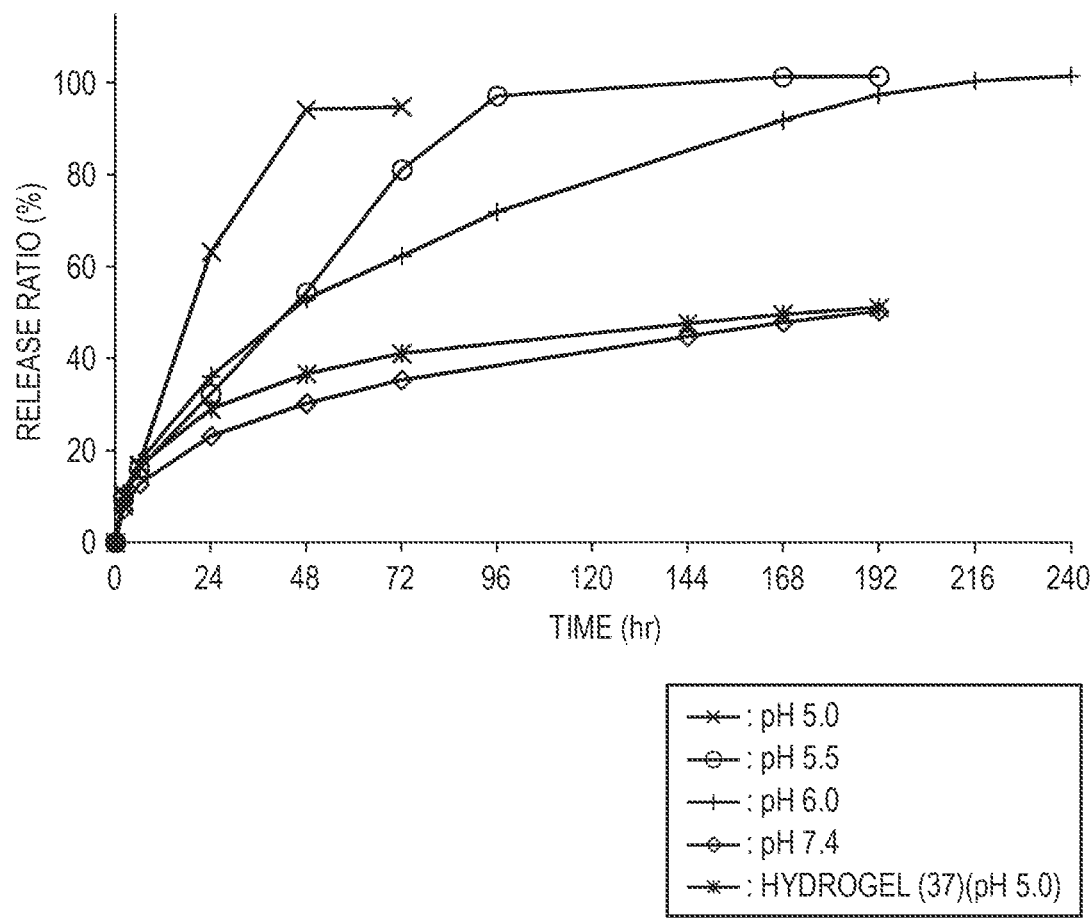
FIG. 7 shows results of the FITC-Dextran release test with Hydrogel (36) formed by encapsulating FITC-Dextran, as a model drug, into the compound of formula (20) described in Examples performed in citrate buffers of pH 5.0 and 5.5 and phosphate buffers of pH 6.0 and 7.4 at 37° C. In addition.

As shown in FIG. 7, Hydrogel (36) still maintained the model drug encapsulated even after the elapse of 192 hours at pH of 7.4, but at lower pH it released the model drug at a different rete corresponding to each pH. On the other hand, Hydrogel (37) of Comparative Example 2 still maintained the model drug encapsulated even after the elapse of 192 hours at pH of 5.0.

While the invention has been described in detail and with reference to specific embodiments thereof, it will be apparent to those skilled in the art that various changes and modifications can be made therein without departing from the spirit and scope of the invention.

This application is based on a Japanese patent application filed on Mar. 31, 2016 (Japanese Patent Application No. 2016-070109), and the whole contents thereof are incorporated herein by reference. Also, all the references cited herein are incorporated as a whole.

The invention claimed is:

1. A hydrogel obtained by crosslinking a polyalkylene glycol derivative having a cyclic benzylidene acetal structure with a crosslinking agent, wherein the polyalkylene glycol derivative having a cyclic benzylidene acetal structure is represented by the following formula (1), and the crosslinking agent is represented by the following formula (2):

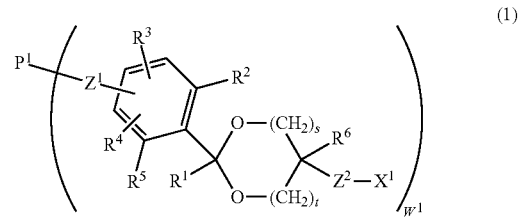

wherein, in the formula (1), $R^1$, $R^2$ and $R^5$ are each independently a hydrogen atom; $R^6$ is a hydrogen atom or a hydrocarbon group; $R^3$ and $R^4$ are each independently a fluorine atom, a chlorine atom, a bromine atom, an iodine atom, or a hydrogen atom; s is 1, t is 0; $P^1$ is represented by the following formula (r3), and all terminals of the polyalkylene glycol constituting $P^1$ are connected to $Z^1$ respectively; $Z^1$ is an ether bond (—O—); $Z^2$ is —$(CH_2)_p$— wherein p is 1 to 4; $W^1$ is 4 and is equal to the number of terminals of the polyalkylene glycol; and $X^1$ is a chemically reactive functional group selected from the group consisting of an active ester group, an active carbonate group and an amino group,

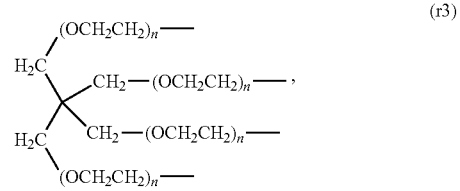

wherein, in the formula (r3), n is 20 to 2,000,

wherein, in the formula (2), $P^2$ is represented by the following formula (s3), and all terminals of the polyalkylene glycol constituting $P^2$ are connected to $Z^3$ respectively; $Z^3$ is $-O(CH_2)_p-$ wherein p is 1 to 5; $W^2$ is an integer of 4 and is equal to the number of terminals of the polyalkylene glycol; and $X^2$ is a chemically reactive functional group selected from the group consisting of an active ester group, an active carbonate group and an amino group,

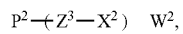  (2)

wherein, in the formula (s3), m is 20 to 2,000.

2. The hydrogel as claimed in claim 1, which further comprises a biofunctional molecule.

* * * * *